(12) United States Patent
Yamashita et al.

(10) Patent No.: US 11,634,608 B2
(45) Date of Patent: Apr. 25, 2023

(54) COMPOUND HAVING ISOCYANURIC SKELETON AND COMPOSITION IN WHICH SAID COMPOUND IS INCLUDED

(71) Applicant: DAIKIN INDUSTRIES, LTD., Osaka (JP)

(72) Inventors: Tsuneo Yamashita, Osaka (JP); Masatoshi Nose, Osaka (JP); Hisashi Mitsuhashi, Osaka (JP); Saya Nii, Osaka (JP); Eiji Sakamoto, Osaka (JP); Kaori Ozawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 53 days.

(21) Appl. No.: 17/210,340

(22) Filed: Mar. 23, 2021

(65) Prior Publication Data

US 2021/0206995 A1 Jul. 8, 2021

Related U.S. Application Data

(63) Continuation of application No. 16/335,729, filed as application No. PCT/JP2017/034376 on Sep. 22, 2017, now Pat. No. 10,988,633.

(30) Foreign Application Priority Data

| Sep. 23, 2016 | (JP) | ................. | 2016-185759 |
| Apr. 20, 2017 | (JP) | ................. | 2017-083841 |
| Jun. 14, 2017 | (JP) | ................. | 2017-116961 |
| Aug. 1, 2017  | (JP) | ................. | 2017-149207 |

(51) Int. Cl.
| C07D 251/34 | (2006.01) |
| C09D 171/02 | (2006.01) |
| C03C 17/32  | (2006.01) |
| C09D 5/00   | (2006.01) |
| C23C 14/12  | (2006.01) |
| C07D 251/10 | (2006.01) |
| C07D 405/14 | (2006.01) |
| C07F 7/18   | (2006.01) |

(52) U.S. Cl.
CPC ............ *C09D 171/02* (2013.01); *C03C 17/32* (2013.01); *C07D 251/10* (2013.01); *C07D 251/34* (2013.01); *C07D 405/14* (2013.01); *C07F 7/1804* (2013.01); *C09D 5/00* (2013.01); *C23C 14/12* (2013.01); *C03C 2217/76* (2013.01); *C03C 2218/151* (2013.01)

(58) Field of Classification Search
CPC .. C07D 251/34; C07D 251/10; C07D 405/14; C09D 171/02; C09D 5/00; C03C 17/32; C03C 2217/76; C03C 2218/151; C07F 7/1804; C23C 14/12

See application file for complete search history.

(56) References Cited

U.S. PATENT DOCUMENTS

| 3,629,255 A      | 12/1971 | Beyleveld et al. |
| 7,955,532 B2     |  6/2011 | Liang et al.     |
| 8,609,742 B2     | 12/2013 | Wakita et al.    |
| 8,828,565 B2     |  9/2014 | Sugiura et al.   |
| 9,051,474 B2     |  6/2015 | Jung et al.      |
| 10,125,107 B1 *  | 11/2018 | Miyamura ............... C07C 69/80 |
| 10,988,633 B2 *  |  4/2021 | Yamashita ................ C07F 7/08 |
| 11,118,085 B2 *  |  9/2021 | Nose .................... C09D 171/02 |
| 2004/0181008 A1  |  9/2004 | Hanazawa et al.  |
| 2005/0121644 A1  |  6/2005 | Dams et al.      |
| 2011/0000816 A1  |  1/2011 | Kato et al.      |
| 2011/0065045 A1  |  3/2011 | Qiu et al.       |
| 2012/0156510 A1  |  6/2012 | Okafuji et al.   |

(Continued)

FOREIGN PATENT DOCUMENTS

| CN | 105658699 A | 6/2016 |
| CN | 106432686 A | 2/2017 |

(Continued)

OTHER PUBLICATIONS

International Search Report for PCT/JP2017/034366 dated Dec. 26, 2017 [PCT/ISA/210].
International Search Report for PCT/JP2017/034376 dated Nov. 28, 2017 [PCT/ISA/210].
International Preliminary Report on Patentability with English Translation of Written Opinion dated Mar. 26, 2019 on PCT/JP2017/034376.
Extended European Search Report dated Jun. 5, 2020, from the European Patent Office in Application No. 17853178.6.
International Preliminary Report on Patentability with a Translation of Written Opinion in International Application No. PCT/JP2017/034366 dated Mar. 26, 2019.
Communication dated Feb. 20, 2020, from the European Patent Office in European Application No. 17853181.0.

(Continued)

*Primary Examiner* — Alexander R Pagano
(74) *Attorney, Agent, or Firm* — Sughrue Mion, PLLC

(57) ABSTRACT

A compound represented by the following formula (1):

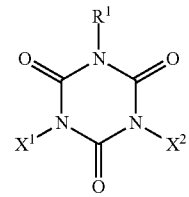

wherein $R^1$ is a monovalent organic group containing a polyether chain; $X^1$ and $X^2$ are each individually a monovalent group; and the polyether chain is a chain represented by the following formula: $-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$, wherein m11, m12, m13, m14, m15, and m16 are each individually an integer of 0 or 1 or greater; $X^{10}$s are each individually H, F, or Cl; the repeating units are present in any order; and the sum of m11 to m16 is an integer of 10 or greater, $R^1$ being other than those containing a urethane bond.

12 Claims, No Drawings

(56) References Cited

U.S. PATENT DOCUMENTS

| | | | |
|---|---|---|---|
| 2012/0231297 A1* | 9/2012 | Sugiura | C10M 107/38 |
| | | | 428/836 |
| 2013/0084458 A1 | 4/2013 | Yamada et al. | |
| 2013/0345040 A1 | 12/2013 | Lee et al. | |
| 2015/0093561 A1 | 4/2015 | Tokunaga et al. | |
| 2016/0002488 A1 | 1/2016 | Takao et al. | |
| 2016/0237199 A1 | 8/2016 | Yoshida et al. | |
| 2019/0322893 A1 | 10/2019 | Nose et al. | |
| 2020/0095433 A1 | 3/2020 | Mitsuhashi et al. | |
| 2020/0157376 A1 | 5/2020 | Hoshino et al. | |
| 2021/0206690 A1* | 7/2021 | Nose | C03C 17/30 |
| 2021/0206994 A1* | 7/2021 | Nose | C08G 65/336 |

FOREIGN PATENT DOCUMENTS

| | | |
|---|---|---|
| JP | 2005-47880 A | 2/2005 |
| JP | 2010-260193 A | 11/2010 |
| JP | 2011-518231 A | 6/2011 |
| JP | 2012-184339 A | 9/2012 |
| JP | 2012-207169 A | 10/2012 |
| JP | 2013-076029 A | 4/2013 |
| JP | 2014-24288 A | 2/2014 |
| JP | 2014-218444 A | 11/2014 |
| JP | 2014-218548 A | 11/2014 |
| JP | 2016-027170 A | 2/2016 |
| JP | 6182291 B1 | 7/2017 |
| JP | 2017-159698 A | 8/2017 |
| KR | 10-2014-0018556 A | 2/2014 |
| WO | 03/002628 A1 | 1/2003 |
| WO | 2014/025716 A1 | 2/2014 |
| WO | 2015/056744 A1 | 4/2015 |

OTHER PUBLICATIONS

Non-Final Office Action dated Oct. 9, 2020, issued by the USPTO in related U.S. Appl. No. 16/335,726.

Office Action dated Mar. 2, 2021, issued by the USPTO in related U.S. Appl. No. 16/335,726.

CAS Abstract and Indexed Compound US 2004/0181008 (2004) (Year: 2004).

CAS Abstract and Additional Indexed Compounds, US 2004/0181008 (2004) (Year: 2004).

CAS Abstract and Indexed Compounds U.S. Pat. No. 7,955,532 (2011) (Year: 2011).

CAS Abstract and Indexed Compound JP 2005047880 (2005) (Year: 2005).

CAS Abstract T. Hoshino et al., US 2020/0157376 (2020) (Year: 2020).

English Language Machine Translation of JP 2017-159698 (2017) (Year: 2017).

* cited by examiner

COMPOUND HAVING ISOCYANURIC SKELETON AND COMPOSITION IN WHICH SAID COMPOUND IS INCLUDED

CROSS REFERENCE TO RELATED APPLICATIONS

This application is a Rule 53(b) Continuation Application of U.S. application Ser. No. 16/335,729, filed on Mar. 22, 2019, which is a National Stage of International Application No. PCT/JP2017/034376, filed on Sep. 22, 2017 which claims priority from Japanese Patent Application No. 2016-185759, filed on Sep. 23, 2016, Japanese Patent Application No. 2017-083841, filed on Apr. 20, 2017, Japanese Patent Application No. 2017-116961, filed on Jun. 14, 2017, and Japanese Patent Application No. 2017-149207, filed on Aug. 1, 2017, the disclosures of which are incorporated herein by reference in their respective entireties.

TECHNICAL FIELD

The invention relates to novel compounds each containing an isocyanuric skeleton and compositions each containing any of the novel compounds.

BACKGROUND ART

Certain fluorine-containing silane compounds are known to provide excellent properties such as water repellency, oil repellency, and antifouling performance when used for surface treatment of substrates. A layer formed by a surface treatment agent containing a fluorine-containing silane compound (hereinafter, also referred to as a "surface treatment layer") is provided, as what is called a functional thin film, for a wide variety of substrates such as glass, plastic, fiber, and building materials.

Patent Literature 1 discloses an antifouling coating agent containing an isocyanuric acid compound represented by the following formula:

[Chem. 1]

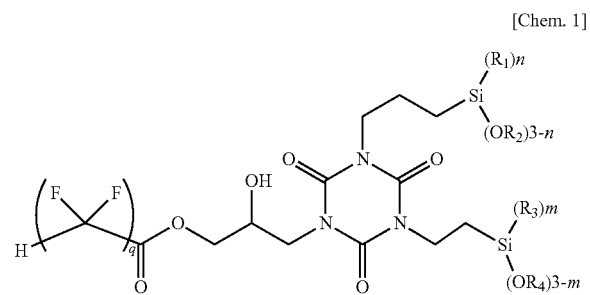

wherein $R_1$, $R_2$, $R_3$, and $R_4$ are each individually a C1-C6 alkyl group; n and m are each individually an integer of 0 to 2; and q is an integer of 1 to 20.

CITATION LIST

Patent Literature

Patent Literature 1: KR 10-2014-0018556 A

SUMMARY OF INVENTION

Technical Problem

There is always a demand for novel antifouling agents for giving excellent antifouling performance to a wide variety of substrates.

In view of the above current state of the art, the invention aims to provide a novel compound to be suitably used for antifouling agents.

Solution to Problem

The invention relates to a compound represented by the following formula (1).
The formula (1) is as follows:

[Chem. 2]

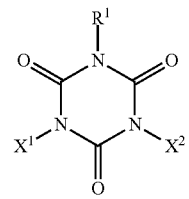

wherein $R^1$ is a monovalent organic group containing a polyether chain; $X^1$ and $X^2$ are each individually a monovalent group; and the polyether chain is a chain represented by the following formula:

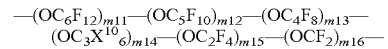

wherein m11, m12, m13, m14, m15, and m16 are each individually an integer of 0 or 1 or greater; $X^{10}$s are each individually H, F, or Cl; and the repeating units are present in any order.

Preferably, at least one or both of $X^1$ and $X^2$ are each individually a monovalent organic group containing a polyether chain, and the polyether chain is a chain represented by the following formula:

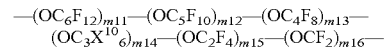

wherein m11, m12, m13, m14, m15, and m16 are each individually an integer of 0 or 1 or greater; $X^{10}$s are each individually H, F, or Cl; and the repeating units are present in any order.

$X^1$ is preferably a monovalent crosslinkable group.
$X^2$ is preferably a monovalent crosslinkable group.
$X^1$ and $X^2$ are preferably each individually a monovalent crosslinkable group.

Preferably, $X^1$ is a monovalent crosslinkable group containing a polyether chain, and the polyether chain is a chain represented by the following formula:

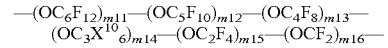

wherein m11, m12, m13, m14, m15, and m16 are each individually an integer of 0 or 1 or greater; $X^{10}$s are each individually H, F, or Cl; and the repeating units are present in any order.

Preferably, $X^2$ is a monovalent crosslinkable group containing a polyether chain, and the polyether chain is a chain represented by the following formula:

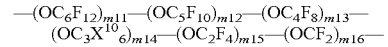

wherein m11, m12, m13, m14, m15, and m16 are each individually an integer of 0 or 1 or greater; $X^{10}$s are each individually H, F, or Cl; and the repeating units are present in any order.

Preferably, $X^1$ and $X^2$ are each individually a monovalent crosslinkable group containing a polyether chain, and the polyether chain is a chain represented by the following formula:

$$-(OC_6F_{12})_{m11}-(OC_5F_{10})_{m12}-(OC_4F_8)_{m13}-$$
$$(OC_3X^{10}{}_6)_{m14}-(OC_2F_4)_{m15}-(OCF_2)_{m16}-$$

wherein m11, m12, m13, m14, m15, and m16 are each individually an integer of 0 or 1 or greater; $X^{10}$s are each individually H, F, or Cl; and the repeating units are present in any order.

The crosslinkable group is preferably at least one crosslinkable group selected from the group consisting of a monovalent Si-containing group, an acryloyl group, a methacryloyl group, an epoxy group, a glycidyl group, an oxetane group, an isocyanate group, a vinyl group, an allyl group, a vinyloxy group, a carboxyl group, a mercapto group, an amino group, a hydroxy group, a phosphonyl group, a cyclic acid anhydride group, a lactone group, a lactam group, a —OC(O)Cl group, a triazine group, an imidazole group, a conjugated olefin group, an acetylene group, a diazo group, an aldehyde group, a ketone group, an alkylboron group, an alkylaluminum group, an alkyltin group, an alkylgermanium group, an alkylzircon group, and a monovalent group containing any of these groups.

$X^1$ is preferably at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

$X^2$ is preferably at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

$X^1$ and $X^2$ are preferably each individually at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

Advantageous Effects of Invention

The novel compound of the invention has the aforementioned structures, and thus exhibits excellent antifouling performance and can suitably be used for antifouling agents. The novel compound of the invention also exhibits excellent releasability and can suitably be used for release agents.

DESCRIPTION OF EMBODIMENTS

The invention will be specifically described hereinbelow.
The compound of the invention is represented by the following formula (1).
The formula (1) is as follows:

[Chem. 3]

wherein $R^1$ is a monovalent organic group containing a polyether chain; $X^1$ and $X^2$ are each individually a monovalent group; and the polyether chain is a chain represented by the following formula:

$$-(OC_6F_{12})_{m11}-(OC_5F_{10})_{m12}-(OC_4F_8)_{m13}-$$
$$(OC_3X^{10}{}_6)_{m14}-(OC_2F_4)_{m15}-(OCF_2)_{m16}-$$

wherein m11, m12, m13, m14, m15, and m16 are each individually an integer of 0 or 1 or greater; $X^{10}$s are each individually H, F, or Cl; and the repeating units are present in any order.

$R^1$ is preferably a monovalent organic group containing a polyether chain other than those containing a urethane bond.

$X^{10}$s are each preferably F.

In the formula, m11 to m16 are each preferably an integer of 0 to 200, more preferably an integer of 0 to 100. The sum of m11 to m16 is preferably an integer of 1 or greater, more preferably an integer of 5 or greater, still more preferably an integer of 10 or greater. The sum of m11 to m16 is preferably an integer of 200 or smaller, more preferably an integer of 100 or smaller. The sum of m11 to m16 is preferably an integer of 10 to 200, more preferably an integer of 10 to 100.

Each repeating unit in the polyether chain may be linear or branched, and is preferably linear. For example, the repeating unit —(OC$_6$F$_{12}$)— may be —(OCF$_2$CF$_2$CF$_2$CF$_2$CF$_2$CF$_2$)—, —(OCF(CF$_3$)CF$_2$CF$_2$CF$_2$CF$_2$)—, —(OCF$_2$CF(CF$_3$)CF$_2$CF$_2$CF$_2$)—, —(OCF$_2$CF$_2$CF(CF$_3$)CF$_2$CF$_2$)—, —(OCF$_2$CF$_2$CF$_2$CF(CF$_3$)CF$_2$)—, or —(OCF$_2$CF$_2$CF$_2$CF$_2$CF(CF$_3$))—, and is preferably —(OCF$_2$CF$_2$CF$_2$CF$_2$CF$_2$CF$_2$)—. The repeating unit —(OC$_5$F$_{10}$)— may be —(OCF$_2$CF$_2$CF$_2$CF$_2$CF$_2$)—, —(OCF(CF$_3$)CF$_2$CF$_2$CF$_2$)—, —(OCF$_2$CF(CF$_3$)CF$_2$CF$_2$)—, —(OCF$_2$CF$_2$CF(CF$_3$)CF$_2$)—, or —(OCF$_2$CF$_2$CF$_2$CF(CF$_3$))—, and is preferably —(OCF$_2$CF$_2$CF$_2$CF$_2$CF$_2$)—. The repeating unit —(OC$_4$F$_8$)— may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$—, and —$(OCF_2CF(C_2F_5))$—, and is preferably —$(OCF_2CF_2CF_2)$—. The repeating unit —$(OC_3F_6)$— may be any of —$(OCF_2CF_2CF_2)$—, —$(OCF(CF_3)CF_2)$—, and —$(OCF_2CF(CF_3))$—, and is preferably —$(OCF_2CF_2CF_2)$—. The repeating unit —$(OC_2F_4)$— may be any of —$(OCF_2CF_2)$— and —$(OCF(CF_3))$—, and is preferably —$(OCF_2CF_2)$—.

In an embodiment, the polyether chain is a chain represented by —$(OC_3F_6)_{m14}$— (wherein m14 is an integer of 1 to 200). The polyether chain is preferably a chain represented by —$(OCF_2CF_2CF_2)_{m14}$— (wherein m14 is an integer of 1 to 200) or a chain represented by —$(OCF(CF_3)CF_2)_{m14}$— (wherein m14 is an integer of 1 to 200), more preferably a chain represented by —$(OCF_2CF_2CF_2)_{m14}$— (wherein m14 is an integer of 1 to 200). In the formula, m14 is preferably an integer of 5 to 200, more preferably an integer of 10 to 200.

In another embodiment, the polyether chain is a chain represented by —$(OC_4F_8)_{m13}$—$(OC_3F_6)_{m14}$—$(OC_2F_4)_{m15}$—$(OCF_2)_{m16}$— (wherein m13 and m14 are each an integer of 0 to 30; m15 and m16 are each an integer of 1 to 200; the sum of m13 to m16 is an integer of 5 or greater; and the repeating units are present in any order). In the formula, m15 and m16 are each preferably an integer of 5 to 200, more preferably an integer of 10 to 200. The sum of m13 to m16 is an integer of 10 or greater. The polyether chain is preferably —$(OCF_2CF_2CF_2CF_2)_{m13}$—$(OCF_2CF_2CF_2)_{m14}$—$(OCF_2CF_2)_{m15}$—$(OCF_2)_{m16}$—. In an embodiment, the polyether chain may be a chain represented by —$(OC_2F_4)_{m15}$—$(OCF_2)_{m16}$— (wherein m15 and m16 are each an integer of 1 to 200; and the repeating units are present in any order). In the formula, m15 and m16 are each preferably an integer of 5 to 200, more preferably an integer of 10 to 200.

In still another embodiment, the polyether chain is a group represented by —$(R^{m1}—R^{m2})_{m17}$—. In the formula, $R^{m1}$ is $OCF_2$ or $OC_2F_4$, preferably $OC_2F_4$. In the formula, $R^{m2}$ is a group selected from $OC_2F_4$, $OC_3F_6$, $OC_4F_8$, $OC_5F_{10}$, and $OC_6F_{12}$ or any combination of two or three groups individually selected from these groups. Preferably, $R^{m1}$ is a group selected from $OC_2F_4$, $OC_3F_6$, and $OC_4F_8$, a group selected from $OC_3F_6$, $OC_4F_8$, $OC_5F_{10}$, and $OC_6F_{12}$, or any combination of two or three groups individually selected from these groups. Examples of the combination of two or three groups individually selected from $OC_2F_4$, $OC_3F_6$, and $OC_4F_8$ include, but are not limited to, —$OC_2F_4OC_3F_6$—, —$OC_2F_4OC_4F_8$—, —$OC_3F_6OC_2F_4$—, —$OC_3F_6OC_3F_6$—, —$OC_4F_8OC_4F_8$—, —$OC_4F_8OC_3F_6$—, —$OC_4F_8OC_2F_4$—, —$OC_2F_4OC_2F_4OC_3F_6$—, —$OC_2F_4OC_2F_4OC_4F_8$—, —$OC_2F_4OC_3F_6OC_3F_6$—, —$OC_2F_4OC_4F_8OC_2F_4$—, —$OC_3F_6OC_2F_4OC_2F_4$—, —$OC_3F_6OC_2F_4OC_3F_6$—, —$OC_3F_6OC_3F_6OC_2F_4$—, and —$OC_3F_6OC_3F_6OC_2F_4$—, and —$OC_4F_8OC_2F_4OC_2F_4$—. In the formula, m17 is an integer of 2 or greater, preferably an integer of 3 or greater, more preferably an integer of 5 or greater, while an integer of 100 or smaller, preferably an integer of 50 or smaller. In the formula, $OC_2F_4$, $OC_3F_6$, $OC_4F_8$, $OC_5F_{10}$, and $OC_6F_{12}$ each may be linear or branched, and is preferably linear. In this embodiment, the polyether chain is preferably —$(OC_2F_4—OC_3F_6)_{m17}$— or —$(OC_2F_4—OC_4F_8)_{m17}$—.

In the polyether chain, the ratio of m15 to m16 (hereinafter, referred to as "m15/m16 ratio") may be 0.1 to 10, preferably 0.2 to 5, more preferably 0.2 to 2, still more preferably 0.2 to 1.5, further more preferably 0.2 to 0.85.

The polyether chain having an m15/m16 ratio of 10 or smaller can lead to more improved smoothness, friction durability, and chemical resistance (e.g., durability against artificial sweat) of the surface treatment layer. The smaller the m15/m16 ratio is, the more the smoothness and friction durability of the surface treatment layer are improved. The polyether chain having an m15/m16 ratio of 0.1 or higher can lead to much better stability of the compound. The higher the m15/m16 ratio is, the more the stability of the compound is improved.

The polyether chain may be at least one chain selected from the group consisting of:

a chain represented by the following formula:

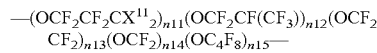
—$(OCF_2CF_2CX^{11}_2)_{n11}(OCF_2CF(CF_3))_{n12}(OCF_2CF_2)_{n13}(OCF_2)_{n14}(OC_4F_8)_{n15}$— wherein n11, n12, n13, n14, and n15 are each individually an integer of 0 or 1 or greater; $X^{11}$s are each individually H, F, or Cl; and the repeating units are present in any order; and a chain represented by the following formula:

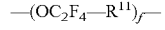
—$(OC_2F_4—R^{11})_f$— wherein $R^{11}$ is a group selected from $OC_2F_4$, $OC_3F_6$, and $OC_4F_8$; and f is an integer of 2 to 100.

$X^{11}$s are each preferably F.

In the formula, n11 to n15 are each preferably an integer of 0 to 200. The sum of n11 to n15 is preferably an integer of 2 or greater, more preferably an integer of 5 to 300, still more preferably an integer of 10 to 200, particularly preferably an integer of 10 to 100.

$R^{11}$ is a group selected from $OC_2F_4$, $OC_3F_6$, and $OC_4F_8$, or any combination of two or three groups individually selected from these groups. Examples of the combination of two or three groups individually selected from $OC_2F_4$, $OC_3F_6$, and $OC_4F_8$ include, but are not limited to, —$OC_2F_4OC_3F_6$—, —$OC_2F_4OC_4F_8$—, —$OC_3F_6OC_2F_4$—, —$OC_3F_6OC_3F_6$—, —$OC_3F_6OC_4F_8$—, —$OC_4F_8OC_4F_8$—, —$OC_4F_8OC_3F_6$—, —$OC_4F_8OC_2F_4$—, —$OC_2F_4OC_2F_4OC_3F_6$—, —$OC_2F_4OC_2F_4OC_4F_8$—, —$OC_2F_4OC_3F_6OC_2F_4$—, —$OC_2F_4OC_3F_6OC_3F_6$—, —$OC_2F_4OC_4F_8OC_2F_4$—, —$OC_3F_6OC_2F_4OC_2F_4$—, —$OC_3F_6OC_2F_4OC_3F_6$—, —$OC_3F_6OC_2F_4OC_3F_6$—, —$OC_3F_6OC_3F_6OC_2F_4$—, and —$OC_4F_8OC_2F_4OC_2F_4$—. In the formula, f is an integer of 2 to 100, preferably an integer of 2 to 50. In the formula, $OC_2F_4$, $OC_3F_6$, and $OC_4F_8$ each may be linear or branched, and is preferably linear. In this embodiment, —$(OC_2F_4—R^{11})_f$— is preferably —$(OC_2F_4—OC_3F_6)_f$— or —$(OC_2F_4—OC_4F_8)_f$—.

In the compound of the invention, the polyether chain moiety has a number average molecular weight of, for example, 500 to 30,000, preferably 1,500 to 30,000, more preferably 2.000 to 10,000, although not limited thereto. The number average molecular weight is a value determined by $^{19}$F-NMR.

In another embodiment, the number average molecular weight of the polyether chain moiety is 500 to 30,000, preferably 1,000 to 20,000, more preferably 2,000 to 15,000, still more preferably 2,000 to 10,000, and may be 3,000 to 6.000.

In another embodiment, the number average molecular weight of the polyether chain moiety may be 4,000 to 30,000, preferably 5,000 to 10,000, more preferably 6,000 to 10,000.

$R^1$ is preferably a monovalent organic group represented by $R^3$—$(OR^2)_a$-L-, wherein $(OR^2)_a$ is the polyether chain; $R^3$ is an alkyl group or a fluorinated alkyl group; and L is a single bond or a divalent linking group.

$R^3$ preferably contains 1 to 16, preferably 1 to 8 carbon atoms.

$R^3$ may be linear or branched, and is preferably a linear or branched C1-C16 alkyl or fluorinated alkyl group, more preferably a linear or branched C1-C8 alkyl or fluorinated alkyl group, still more preferably a linear or branched C1-C6 alkyl or fluorinated alkyl group, further more preferably a linear or branched C1-C3 alkyl or fluorinated alkyl group, particularly preferably a linear C1-C3 alkyl or fluorinated alkyl group.

$R^3$ is preferably a C1-C16 fluorinated alkyl group, more preferably a $CF_2H-C_{1-15}$ fluoroalkylene group or a C1-C16 perfluoroalkyl group, still more preferably a C1-C16 perfluoroalkyl group.

The C1-C16 perfluoroalkyl group may be linear or branched, and is preferably a linear or branched C1-C6, particularly C1-C3, perfluoroalkyl group, more preferably a linear C1-C3 perfluoroalkyl group, specifically $-CF_3$, $-CF_2CF_3$, or $-CF_2CF_2CF_3$.

L is a single bond or a divalent linking group that directly binds to the ring in the formula (1). L is preferably a single bond, an alkylene group, or a divalent group containing at least one bond selected from the group consisting of an ether bond and an ester bond, more preferably a single bond, a C1-C10 alkylene group, or a C1-C10 divalent hydrocarbon group containing at least one bond selected from the group consisting of an ether bond and an ester bond.

L is still more preferably a group represented by the following formula:

$$-(CX^{121}X^{122})_o-(L^1)_p-(CX^{123}X^{124})_q-$$

wherein $X^{121}$ to $X^{124}$ are each individually H, F, OH, or $-OSi(OR^{121})_3$ (wherein three $R^{121}$s are each individually a C1-C4 alkyl group); $L^1$ is $-C(=O)NH-$, $-NHC(=O)-$, $-O-$, $-C(=O)O-$, $-OC(=O)-$, $-OC(=O)O-$, or $-NHC(=O)NH-$ (wherein the left side of each bond binds to $CX^{121}X^{122}$); o is an integer of 0 to 10; p is 0 or 1; and q is an integer of 1 to 10.

$L^1$ is preferably $-O-$ or $-C(=O)O-$.

L is particularly preferably a group represented by the following formula:

$$-(CF_2)_{m11}-(CH_2)_{m12}-O-(CH_2)_{m13}-$$

wherein m11 is an integer of 1 to 3; m12 is an integer of 1 to 3; and m13 is an integer of 1 to 3;

a group represented by the following formula:

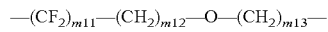
$$-(CF_2)_{m14}-(CH_2)_{m15}-O-CH_2CH(OH)-(CH_2)_{m16}-$$

wherein m14 is an integer of 1 to 3, m15 is an integer of 1 to 3, and m16 is an integer of 1 to 3;

a group represented by the following formula:

$$-(CF_2)_{m17}-(CH_2)_{m18}-$$

wherein m17 is an integer of 1 to 3; and m18 is an integer of 1 to 3; or a group represented by the following formula:

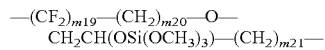
$$-(CF_2)_{m19}-(CH_2)_{m20}-O-CH_2CH(OSi(OCH_3)_3)-(CH_2)_{m21}-$$

wherein m19 is an integer of 1 to 3; m20 is an integer of 1 to 3; and m21 is an integer of 1 to 3.

Specific examples of L include, but are not limited to, $-C_2H_4-$, $-C_3H_6-$, $-C_4H_8-O-CH_2-$, $-CO-CH_2-CH(OH)-CH_2-$, $-(CF_2)_n-$ (wherein n is an integer of 0 to 4), $-CH_2-$, $-C_4H_8-$, $-(CF_2)_n-(CH_2)_m-$ (wherein n and m are each individually an integer of 0 to 4), $-CF_2CF_2CH_2OCH_2CH(OH)CH_2-$, and $-CF_2CF_2CH_2OCH_2CH(OSi(OCH_3)_3)CH_2-$.

At least one or both of $X^1$ and $X^2$ may each individually be a monovalent organic group containing the polyether chain. Preferred groups for this organic group are the same as those for $R^1$.

$X^1$ may be a monovalent crosslinkable group.

$X^2$ may be a monovalent crosslinkable group.

$X^1$ and $X^2$ each may individually be a monovalent crosslinkable group.

The crosslinkable group contributes to the adhesiveness to substrates and contributes to crosslinking reactions. The crosslinkable group may chemically react with a material of the substrate. The crosslinkable group may react with another crosslinkable group, or may react with substances such as a curable resin or a curable monomer to be mentioned later.

The crosslinkable group is preferably a monovalent crosslinkable group having heat-crosslinkability or photo-crosslinkability.

The crosslinkable group is preferably at least one crosslinkable group selected from the group consisting of a monovalent Si-containing group, an acryloyl group, a methacryloyl group, an epoxy group, a glycidyl group, an oxetane group, an isocyanate group, a vinyl group, an allyl group, a vinyloxy group, a carboxyl group, a mercapto group, an amino group, a hydroxy group, a phosphonyl group, a cyclic acid anhydride group, a lactone group, a lactam group, a $-OC(O)Cl$ group, a triazine group, an imidazole group, a conjugated olefin group, an acetylene group, a diazo group, an aldehyde group, a ketone group, an alkylboron group, an alkylaluminum group, an alkyltin group, an alkylgermanium group, an alkylzircon group, and a monovalent group containing any of these groups, more preferably at least one crosslinkable group selected from the group consisting of a monovalent Si-containing group, an acryloyl group, an epoxy group, a glycidyl group, a vinyl group, an allyl group, a hydroxy group, a ketone group, and a monovalent group containing any of these groups.

The "monovalent group containing any of these groups" may be, for example, a monovalent crosslinkable group that contains a hydrocarbon chain containing any of these groups at a side chain end or a main chain end or a monovalent crosslinkable group that contains a polyether chain containing any of these groups at a side chain end or a main chain end.

In other words, $X^1$ may be a monovalent crosslinkable group containing the polyether chain.

$X^2$ may be a monovalent crosslinkable group containing the polyether chain.

Further, $X^1$ and $X^2$ may each individually be a monovalent crosslinkable group containing the polyether chain.

The polyether chain is a chain represented by the following formula:

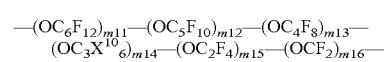
$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein m11, m12, m13, m14, m15, and m16 are each individually an integer of 0 or 1 or greater; $X^{10}$s are each individually H, F, or Cl; and the repeating units are present in any order.

The polyether chain may be at least one chain selected from the group consisting of:

a chain represented by the following formula:

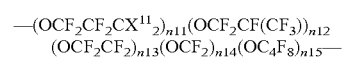
$$-(OCF_2CF_2CX^{11}{}_2)_{n11}(OCF_2CF(CF_3))_{n12}(OCF_2CF_2)_{n13}(OCF_2)_{n14}(OC_4F_8)_{n15}-$$

wherein n11, n12, n13, n14, and n15 are each individually an integer of 0 or 1 or greater; $X^{11}$s are each individually H, F, or Cl; and the repeating units are present in any order; and a chain represented by the following formula:

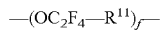

wherein $R^{11}$ is a group selected from $OC_2F_4$, $OC_3F_6$, and $OC_4F_8$; and f is an integer of 2 to 100.

Preferred chains for the polyether chain are the same as those for $R^1$.

The Si-containing group is preferably at least one group selected from the group consisting of a silane-containing reactive crosslinkable group, a silicone residue, a silsesquioxane residue, and a silazane group.

The silane-containing reactive crosslinkable group is preferably a group represented by the following formula:

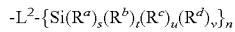

(wherein $L^2$ is a single bond or a divalent linking group; $R^a$, $R^b$, and $R^c$ are the same as or different from each other, and are each hydrogen, a halogen, a C1-C10 alkoxy group, a C1-C10 amino group, a C1-C10 acetoxy group, a C3-C10 allyl group, or a C3-C10 glycidyl group; $R^d$s are the same as or different from each other, and are each —O—, —NH—, —C≡C—, or a silane bond; s, t, and u are the same as or different from each other, and are each 0 or 1; v is an integer of 0 to 3; n is an integer of 1 to 20; when n is 1, (s+t+u) is 3 and v is 0; when n is 2 to 20, the (s+t+u) values are the same as or different from each other and are each 0 to 2, and vs are the same as or different from each other and are each 0 to 2; and when v is an integer of 1 or greater, at least two Si atoms are bound to each other via $R^d$ in the form of a straight chain, a ladder, a cycle, or a polycycle). $R^a$, $R^b$, and $R^c$ are each a monovalent group binding to Si. $R^d$ is a divalent group binding to two Si atoms.

$R^a$, $R^b$, and $R^c$ are the same as or different from each other. At least one thereof is hydrogen, a halogen, a C1-C10 alkoxy group, or a C1-C10 amino group, while the others thereof are each preferably a C1-C10 acetoxy group, a C3-C10 allyl group, or a C3-C10 glycidyl group, still more preferably a C1-C4 alkoxy group. When n is 2 to 20, preferably, the (s+t+u) values are the same as or different from each other and are each 0 to 2, and v is 0 to 2.

In $R^a$, $R^b$, and $R^c$, the halogen is preferably Cl, Br, or I, more preferably Cl.

In $R^a$, $R^b$, and $R^c$, the alkoxy group preferably contains 1 to 5 carbon atoms. The alkoxy group may be linear, cyclic, or branched. Any of the hydrogen atoms may be replaced by a different atom such as a fluorine atom. The alkoxy group is preferably a methoxy, ethoxy, propyloxy, or butoxy group, more preferably a methoxy or ethoxy group.

$R^d$s are the same as or different from each other, and are each —O—, —NH—, —C≡C—, or a silane bond. $R^d$s are each preferably —O—, —NH—, or —C≡C—. $R^d$s are each a divalent group binding to two Si atoms, and $R^d$ allows two or more silicon atoms to bind to each other via $R^d$ in the form of a straight chain, a ladder, a cycle, or a polycycle. When n is an integer of 2 or greater, the silicon atoms themselves may bind to each other.

$R^d$s may be the same as or different from each other, and each may be a group represented by —Z—$SiR^{d1}_p R^{d2}_q R^{d3}_r$—.

In the formula, Zs are the same as or different from each other, and are each a single bond or a divalent linking group.

Specific examples of Z include —$C_2H_4$—, —$C_3H_6$—, —CO—O—$CH_2$—CH(OH)—$CH_2$—, —$CH_2$—, and —$C_4H_8$—.

In the formula, $R^{d1}$s are the same as or different from each other, and are each $R^{d1}$. $R^{d1}$ is defined in the same manner as $R^d$.

The number of Si atoms linearly linked via the Z group in $R^d$ is at most five. In other words, when at least one $R^{d1}$ is present in $R^d$, there are two or more Si atoms linearly linked via the Z group in $R^d$, and the number of Si atoms linearly linked via such a Z group is at most five. The "number of Si atoms linearly linked via the Z group in $R^d$" is equivalent to the number of repeated —Z—Si— units linearly linked in $R^d$.

An example of linking of Si atoms via the Z group in $R^d$ is shown below.

[Chem. 4]

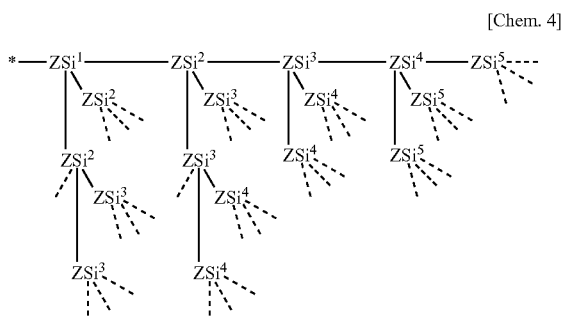

In the formula, the symbol * represents the site binding to Si in the main chain; and the symbol ••• represents binding of a predetermined group other than ZSi. In other words, when all of the three bindings of a Si atom are represented by the symbol •••, it means the site where repeat of ZSi is finished. The superscript immediately after Si is the number of Si atoms linearly linked from the symbol * via the Z group. In other words, when the ZSi repeating is finished at $Si^2$, the chain is considered as including two "Si atoms linearly linked via the Z group in $R^d$". Similarly, when ZSi repeating is finished at $Si^3$, $Si^4$, and $Si^5$, the chain includes three, four, and five "Si atoms linearly linked via the Z group in $R^d$", respectively. As is clear from the above formula, a plurality of ZSi chains is present in $R^d$. Still, they need not to be the same length, and may have the respective lengths.

In a preferred embodiment, as shown below, the "number of Si atoms linearly linked via the Z group in $R^d$" is one (left formula) or two (right formula) in all the chains.

[Chem. 5]

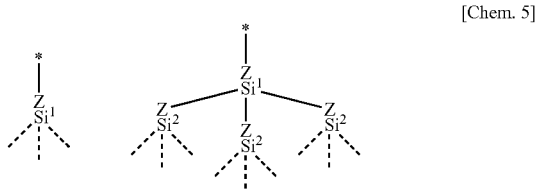

In an embodiment, the number of Si atoms linearly linked via the Z group in $R^d$ is one or two, preferably one.

In the formula, $R^{d2}$s are the same as or different from each other, and are each a hydroxy group or a hydrolyzable group. The hydroxy group may be, but is not limited to, a group generated by hydrolysis of a hydrolyzable group.

$R^{d2}$ is preferably —OR, wherein R is a substituted or unsubstituted $C_{1-3}$ alkyl group, more preferably a methyl group.

In the formula, $R^{d3}$s are the same as or different from each other, and are each a hydrogen atom or a lower alkyl group. The lower alkyl group is preferably a C1-C20 alkyl group, more preferably a C1-C6 alkyl group, still more preferably a methyl group.

In the formula, ps are the same as or different from each other, and are each an integer of 0 to 3; qs are the same as or different from each other, and are each an integer of 0 to 3; and rs are the same as or different from each other, and are each an integer of 0 to 3. The sum of p', q', and r' is 3.

In a preferred embodiment, q' in the terminal $R^{d1}$ in $R^d$ (or $R^d$, if $R^{d1}$ is absent) is preferably 2 or greater, such as 2 or 3, more preferably 3.

In a preferred embodiment, $R^d$ may contain, at an end thereof, at least one $-Si(-Z-SiR^{d2}{}_qR^{d3}{}_{r'})_2$ or $-Si(-Z-SiR^{d2}{}_qR^{d3}{}_{r'})_3$, preferably $-Si(-Z-SiR^{d2}{}_q'R^{d3}{}_{r'})_3$. In the formula, the $(-Z-SiR^{d2}{}_qR^{d3}{}_{r'})$ unit is preferably $(-Z-SiR^{d2}{}_3)$. In a more preferred embodiment, all the ends of $R^d$ are preferably $-Si(-Z-SiR^{d2}{}_qR^{d3}{}_{r'})_3$, and may be more preferably $-Si(-Z-SiR^{d2}{}_3)_3$.

In order to improve the crosslinkability, the silane-containing reactive crosslinkable group also preferably contains a C1-C5 allyl group, a C1-C5 glycidyl group, an acryl group, or a methacryl group. In other words, in the silane-containing reactive crosslinkable group, at least one of $R^a$, $R^b$, and $R^c$ is preferably a C1-C5 allyl group, a C1-C5 glycidyl group, an acryl group, or a methacryl group.

$L^2$ is a single bond or a divalent linking group that directly binds to the ring in the formula (1). $L^2$ is preferably a single bond, an alkylene group, or a divalent group containing at least one bond selected from the group consisting of ether bond and ester bond, more preferably a single bond, a C1-C10 alkylene group, or a C1-C10 divalent hydrocarbon group containing at least one bond selected from the group consisting of ether bond and ester bond.

Specific examples of $L^2$ include $-C_2H_4-$, $-C_3H_6-$, $-C_4H_8-O-CH_2-$, $-CO-O-CH_2-CH(OH)-CH_2-$, $-CH_2-$, and $-C_4H_8-$.

Examples of the silane-containing reactive crosslinkable group include $-L^2-SiR^5{}_3$, $-L^2-Si(OR^6)_3$, $-L^2-Si(NR^6{}_2)_3$, and $-L^2-Si(OCOR^6)_3$, wherein $L^2$ is defined in the same manner as mentioned above; $R^5$ is a halogen atom; and $R^6$s are each individually a C1-C4 alkyl group.

Examples of the silicone residue include the following.

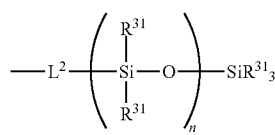
[Chem. 6]

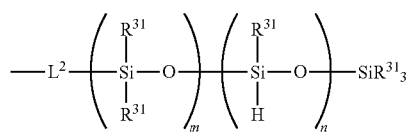
[Chem. 7]

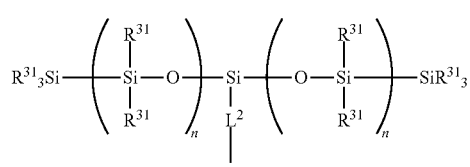
[Chem. 8]

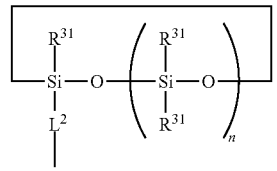
[Chem. 9]

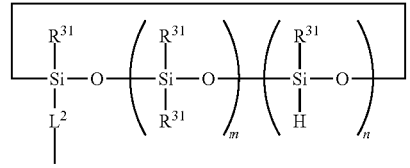
[Chem. 10]

In the formulae, $L^2$ is a single bond or a divalent linking group; n is an integer of 1 to 20; m is an integer of 0 to 10; $R^{31}$s are each individually a monovalent group; and at least one $R^{31}$ in each group is a reactive group.

$R^{31}$s in each group are each individually a monovalent group, and may be the above reactive group or a group other than the above reactive group. At least one $R^{31}$ in each group needs to be the above reactive group.

The reactive group is preferably at least one selected from the group consisting of H, a halogen atom, $-OR^{32}$ (wherein $R^{32}$ is a C1-C4 alkyl group or a C6-C20 aryl group), $-L^3-SiR^5{}_3$ (wherein $L^3$ is a single bond or a C1-C10 alkylene group; and $R^5$ is a halogen atom), $-L^3-Si(OR^6)_3$ (wherein $L^3$ is defined in the same manner as mentioned above; and $R^6$s are each individually a C1-C4 alkyl group), $-L^3-Si(NR^6{}_2)_3$ (wherein $L^3$ and $R^6$ are defined in the same manner as mentioned above), $-L^3-Si(OCOR^6)_3$ (wherein $L^3$ and $R^6$ are defined in the same manner as mentioned above), and a group containing any of these groups.

The group other than the above reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, $-CONR^kCOR^l$ (wherein $R^k$ and $R^l$ are each individually H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

Examples of the silicone residue also include the following.

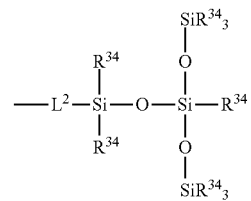
[Chem. 11]

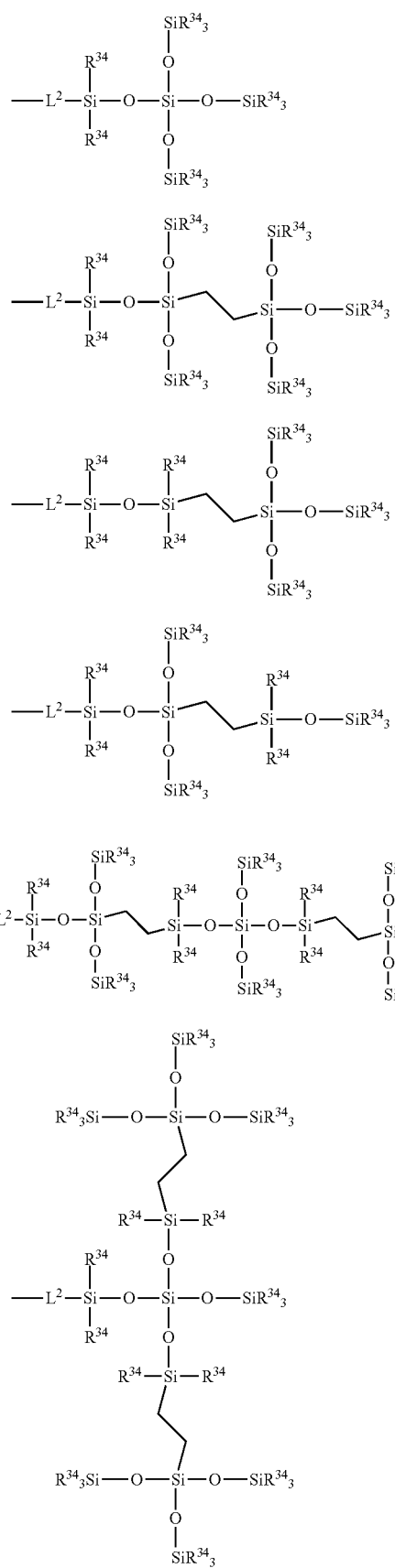

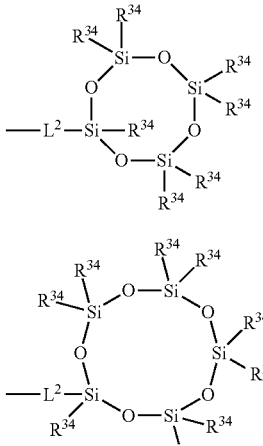

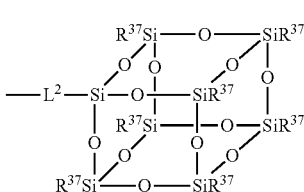

In the formulae, $L^2$ is a single bond or a divalent linking group; $R^{34}$s are each individually a monovalent group; and at least one $R^{34}$ in each group is a reactive group.

$R^{34}$s in each group are each individually a monovalent group, and may be the above reactive group or a group other than the above reactive group. At least one $R^{34}$ in each group needs to be the above reactive group.

The reactive group is preferably at least one selected from the group consisting of —H, —OR$^{35}$ (wherein $R^{35}$ is a C1-C4 alkyl group), a halogen atom, —OH, —O—CR$^{35}$=CH$_2$ (wherein $R^{35}$ is defined in the same manner as mentioned above), —OCOR$^{35}$ (wherein $R^{35}$ is defined in the same manner as mentioned above), —OCO-OR$^j$ (wherein $R^j$ is an alkyl group or a halogenated alkyl group), —NR$^{35}_2$ (wherein $R^{35}$ is defined in the same manner as mentioned above), and a group containing any of these groups.

The group other than the above reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —CONR$^k$COR$^l$ (wherein $R^k$ and $R^l$ are each individually H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

Examples of the silsesquioxane residue include the following.

-continued

[Chem. 21]
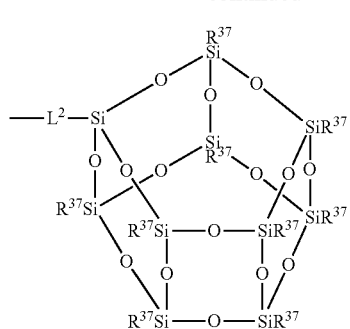

[Chem. 22]
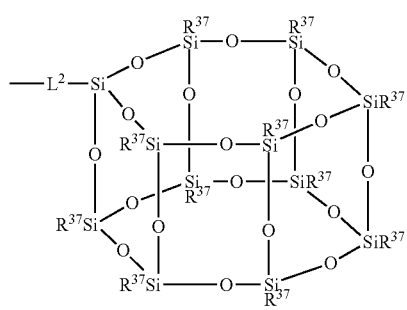

[Chem. 23]
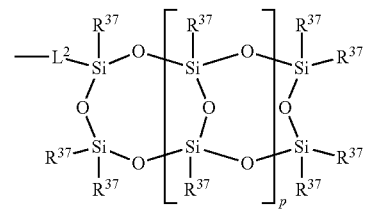

[Chem. 24]
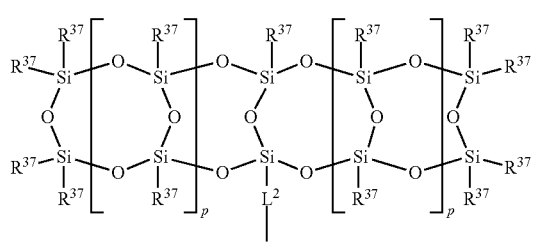

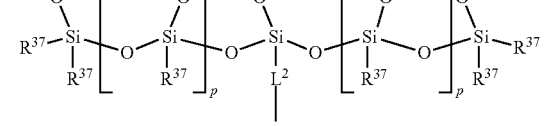

In the formulae, $L^2$ is a single bond or a divalent linking group; $R^{37}$s are each individually a monovalent group; at least one $R^{37}$ in each group is a reactive group; and ps are each individually an integer of 0 to 5000.

$R^{37}$s in each group are each individually a monovalent group, and may be the above reactive group or a group other than the above reactive group. At least one $R^{37}$ in each group needs to be the above reactive group.

The reactive group is preferably at least one selected from the group consisting of —H, —$OR^{35}$ (wherein $R^{35}$ is a C1-C4 alkyl group), a halogen atom, —OH, —O—$CR^{35}$=$CH_2$ (wherein $R^{35}$ is defined in the same manner as mentioned above), —$OCOR^{35}$ (wherein $R^{35}$ is defined in the same manner as mentioned above), —OCO-$OR^j$ (wherein $R^j$ is an alkyl group or a halogenated alkyl group), —$NR^{35}_2$ (wherein $R^{35}$ is defined in the same manner as mentioned above), and a group containing any of these groups.

The group other than the above reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$CONR^kCOR^l$ (wherein $R^k$ and $R^l$ are each individually H, an alkyl group, or a halogenated alkyl group), a glycan-containing group, an alkylene polyether group, an arene group, a halogenated arene group, a heterocycle-containing group, an aryl group, and a halogenated aryl group.

$L^2$ is a single bond or a divalent linking group that directly binds to the ring in the formula (1). Preferred examples of $L^2$ include those as mentioned above.

One or both of $X^1$ and $X^2$ may be each a group that is neither the above monovalent organic group containing a polyether chain nor the above crosslinkable group.

In other words, $X^1$ may be at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$OCOOR^j$, wherein $R^j$ is an alkyl group or a halogenated alkyl group, —$CONR^kCOR^l$, wherein $R^k$ and $R^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

$X^2$ may be at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$OCOOR^j$, wherein $R^j$ is an alkyl group or a halogenated alkyl group, —$CONR^kCOR^l$, wherein $R^k$ and $R^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

Further, $X^1$ and $X^2$ may each individually be at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$OCOOR^j$, wherein $R^j$ is an alkyl group or a halogenated alkyl group, —$CONR^kCOR^l$, wherein $R^k$ and $R^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

Examples of the silicone residue other than those containing a reactive group include the following groups. The reactive group means those mentioned as examples of the reactive group which may constitute $R^{37}$.

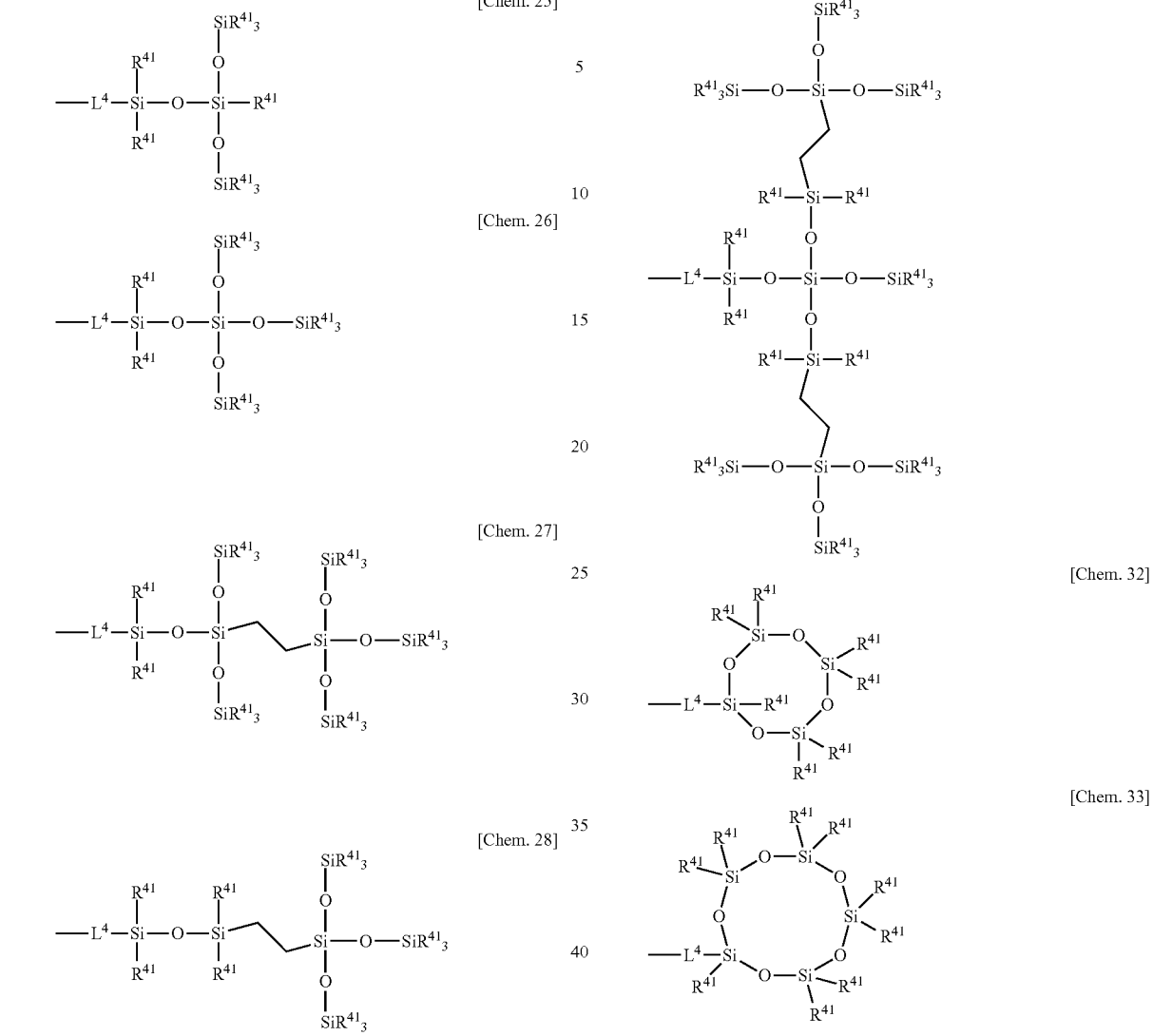

In the formulae, $L^4$ is a single bond or a divalent linking group; and $R^{41}$s are each individually a monovalent group other than the reactive group.

The group other than the above reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$CONR^kCOR^l$ (wherein $R^k$ and $R^l$ are each individually H, an alkyl group, or a halogenated alkyl group), a glycan-containing group, an alkylene polyether group, an arene group, a halogenated arene group, a heterocycle-containing group, an aryl group, and a halogenated aryl group.

$L^4$ is a single bond or a divalent linking group that directly binds to the ring in the formula (1). $L^4$ is preferably a single bond, an alkylene group, or a divalent group containing at least one bond selected from the group consisting of ether bond and ester bond, more preferably a single bond, a C1-C10 alkylene group, or a C1-C10 divalent hydrocarbon group containing at least one bond selected from the group consisting of ether bond and ester bond.

Specific examples of $L^4$ include —$C_2H_4$—, —$C_3H_6$—, —$C_4H_8$—O—$CH_2$—, and —CO—O—$CH_2$—CH(OH)—$CH_2$—.

Examples of the silsesquioxane residue other than those containing a reactive group include the following groups. The reactive group means those mentioned as examples of the reactive group which may constitute $R^{37}$.

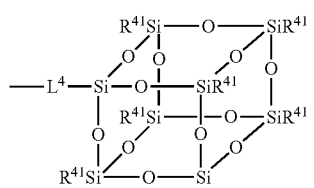
[Chem. 34]

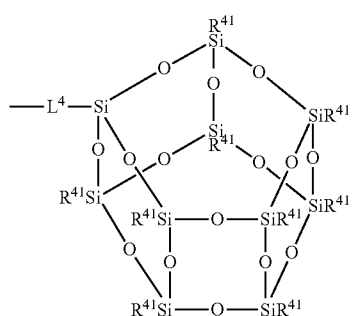
[Chem. 35]

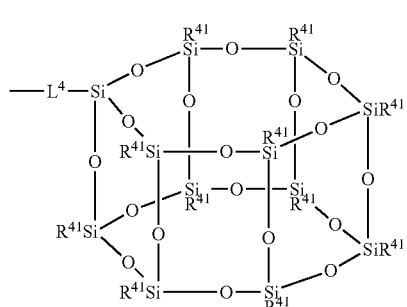
[Chem. 36]

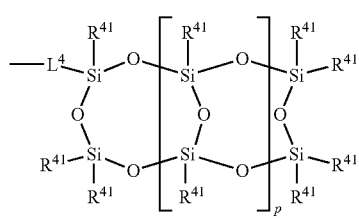
[Chem. 37]

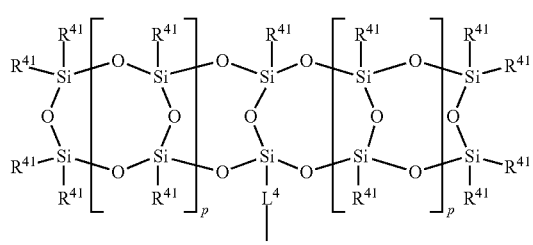
[Chem. 38]

In the formulae, $L^4$ is a single bond or a divalent linking group; $R^{41}$s are each individually a monovalent group other than the reactive group; and ps are each individually an integer of 0 to 5000.

The group other than the above reactive group is preferably at least one selected from the group consisting of an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —$CONR^kCOR^l$ (wherein $R^k$ and $R^l$ are each individually H, an alkyl group, or a halogenated alkyl group), a glycan-containing group, an alkylene polyether group, an arene group, a halogenated arene group, a heterocycle-containing group, an aryl group, and a halogenated aryl group.

$L^4$ is a single bond or a divalent linking group that directly binds to the ring in the formula (1). Preferred examples of $L^4$ include those as mentioned above.

Examples of the silazane group include the following groups.

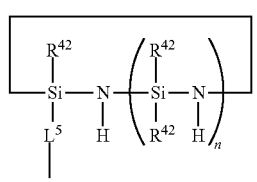
[Chem. 39]

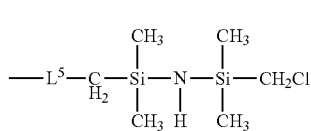
[Chem. 40]

In the formulae, $L^5$ is a single bond or a divalent linking group; m is an integer of 2 to 100; n is an integer of 100 or smaller; and $R^{42}$s are each individually H, a C1-C10 alkyl group, an alkenyl group, a C5-C12 cycloalkyl group, a C6-C10 aryl group, an alkylsilyl group, an alkylcyano group, or a C1-C4 alkoxy group.

$L^5$ is a single bond or a divalent linking group that directly binds to the ring in the formula (1). $L^5$ is preferably a single bond, an alkylene group, or a divalent group containing at least one bond selected from the group consisting of ether bond and ester bond, more preferably a single bond, a C1-C10 alkylene group, or a C1-C10 divalent hydrocarbon group containing at least one bond selected from the group consisting of ether bond and ester bond.

Specific examples of $L^5$ include —$C_2H_4$—, —$C_3H_6$—, —$C_4H_8$—O—$CH_2$—, and —CO—O—$CH_2$—CH(OH)—$CH_2$—.

Specific examples of the silazane group include the following groups.

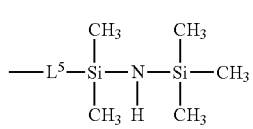
[Chem. 41]

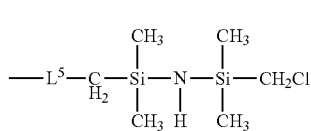
[Chem. 42]

-continued

[Chem. 43]
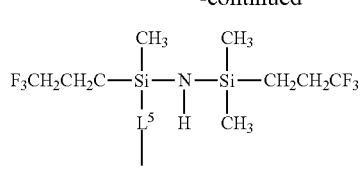

[Chem. 44]
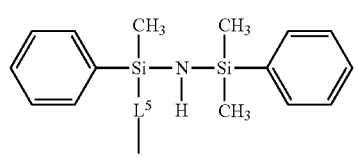

[Chem. 45]
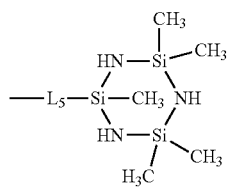

[Chem. 46]
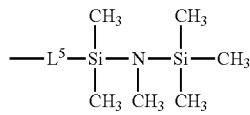

[Chem. 47]
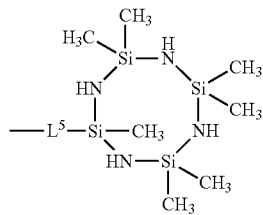

In the compound of the invention, $R^1$ has an average molecular weight of 500 to 30,000, preferably 1,500 to 30,000, more preferably 2,000 to 10,000, although not limited thereto.

The compound of the invention may have an average molecular weight of $5 \times 10^2$ to $1 \times 10^5$, although not limited thereto. In order to achieve good UV resistance and friction durability, the average molecular weight is preferably 2,000 to 30,000, more preferably 2,500 to 12,000. The term "average molecular weight" as used herein means the number average molecular weight, and the "average molecular weight" is a value determined by $^{19}$F-NMR.

Next, a method for producing the compound of the invention is described hereinbelow. The compound of the invention can be produced by reacting an isocyanuric acid derivative compound represented by the following formula:

[Chem. 48]
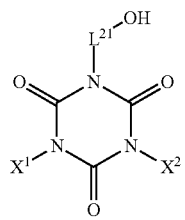

(wherein $X^1$ and $X^2$ are defined in the same manner as mentioned above; and $L^{21}$ is a single bond or a divalent linking group) and a compound represented by $R^{21}$—$X^{21}$ (wherein $R^{21}$ is a monovalent organic group constituting the above $R^1$ together with —O-$L^{21}$-; and $X^{21}$ is Cl, Br, or I).

$R^{21}$ constitutes the above $R^1$ together with —O-$L^{21}$-, and thus naturally contains the polyether chain. This reaction generates a monovalent organic group represented by $R^{21}$—O-$L^{21}$-. $R^{21}$ is more preferably a monovalent organic group represented by $R^3$—$(OR^2)_a$-$L^{22}$-, wherein $(OR^2)_a$ is the polyether chain; $R^3$ is an alkyl or fluorinated alkyl group; and $L^{22}$ is a single bond or a divalent linking group constituting the above L together with —O-$L^{21}$-.

The compound of the invention may also be produced by reacting an isocyanuric acid derivative compound represented by the following formula:

[Chem. 49]
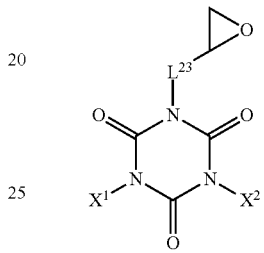

(wherein $X^1$ and $X^2$ are defined in the same manner as mentioned above; and $L^{23}$ is a single bond or a divalent linking group) and a compound represented by $R^{22}$—COOH (wherein $R^{22}$ is a monovalent organic group constituting the above $R^1$ together with —COO—$CH_2CH(OH)$-$L^{23}$-).

$R^{22}$ constitutes the above $R^1$ together with —COO—$CH_2CH(OH)$-$L^{23}$-, and thus naturally contains the polyether chain. This reaction generates a monovalent organic group represented by $R^{22}$—COO—$CH_2CH(OH)$-$L^{23}$-. $R^{22}$ is preferably a monovalent organic group represented by $R^3$—$(OR^2)_a$-$L^{24}$-, wherein $(OR^2)_a$ is the polyether chain; $R^3$ is an alkyl or fluorinated alkyl group; and $L^{24}$ is a single bond or a divalent linking group constituting the above L together with —COO—$CH_2CH(OH)$-$L^{23}$-.

The compound of the invention may also be produced by reacting an isocyanuric acid derivative compound represented by the following formula:

[Chem. 50]
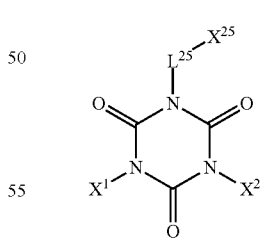

(wherein $X^1$ and $X^2$ are defined in the same manner as mentioned above; $L^{25}$ is a single bond or a divalent linking group; and $X^{25}$ is Cl, Br, or I) and a compound represented by $R^{23}$—OH (wherein $R^{23}$ is a monovalent organic group constituting the above $R^1$ together with —O-$L^{25}$-).

$R^{23}$ constitutes the above $R^1$ together with —O-$L^{25}$-, and thus naturally contains the polyether chain. This reaction generates a monovalent organic group represented by $R^{23}$—O-$L^{25}$-. $R^{23}$ is more preferably a monovalent organic group represented by $R^3$—$(OR^2)_a$-$L^{2S}$-, wherein $(OR^2)_a$ is the polyether chain; $R^3$ is an alkyl or fluorinated alkyl group; and $L^{2S}$ is a single bond or a divalent linking group constituting the above L together with —O-$L^{25}$-.

The compound of the invention may also be produced by reacting an isocyanuric acid derivative compound represented by the following formula:

[Chem. 51]

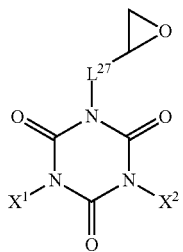

(wherein $X^1$ and $X^2$ are defined in the same manner as mentioned above; and $L^{27}$ is a single bond or a divalent linking group) and a compound represented by $R^{24}$—OH (wherein $R^{24}$ is a monovalent organic group constituting the above $R^1$ together with —O—$CH_2CH(OH)$-$L^{27}$-).

$R^{24}$ constitutes the above $R^1$ together with —O—$CH_2CH(OH)$-$L^{27}$-, and thus naturally contains the polyether chain. This reaction generates a monovalent organic group represented by $R^{24}$—O—$CH_2CH(OH)$-$L^{27}$-. $R^{24}$ is preferably a monovalent organic group represented by $R^3$—$(OR^2)_a$-$L^{28}$-, wherein $(OR^2)_a$ is the polyether chain; $R^3$ is an alkyl or fluorinated alkyl group; and $L^{28}$ is a single bond or a divalent linking group constituting the above L together with —O—$CH_2CH(OH)$-$L^{27}$-.

The compound of the invention may also be produced by reacting an isocyanuric acid derivative compound represented by the following formula:

[Chem. 52]

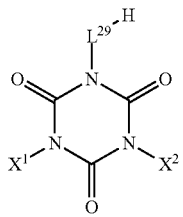

(wherein $X^1$ and $X^2$ are defined in the same manner as mentioned above; and $L^{29}$ is a single bond or a divalent linking group) and a compound represented by $R^{25}$—O—$SO_2R^{2S}$ (wherein $R^{25}$ is a monovalent organic group constituting the above $R^1$ together with -$L^{29}$-; and $R^{2S}$ is an alkyl or fluorinated alkyl group) or a compound represented by $R^{25}$—$X^{2S}$ (wherein $R^{25}$ is defined in the same manner as mentioned above; and $X^{2S}$ is Cl, Br, or I).

$R^{25}$ constitutes the above $R^1$ together with -$L^{29}$-, and thus naturally contains the polyether chain. This reaction generates a monovalent organic group represented by $R^{25}$-$L^{29}$-. $R^{25}$ is more preferably a monovalent organic group represented by $R^3$—$(OR^2)_a$-$L^{30}$-, wherein $(OR^2)_a$ is the polyether chain; $R^3$ is an alkyl or fluorinated alkyl group; and $L^{30}$ is a single bond or a divalent linking group constituting the above L together with -$L^{29}$-.

In any of the above reactions with one or both of $X^1$ and $X^2$ being the above crosslinkable groups, each crosslinkable group may be allowed to react with another compound after the above reaction. For example, when $X^1$ is a group containing a double bond (preferably, an allyl group), the double bond of $X^1$ may be allowed to react with a compound represented by H—$\{Si(R^a)_s(R^b)_t(R^c)_u(R^d)_v\}_n$ (wherein $R^a$, $R^b$, $R^c$, $R^d$, s, t, u, v, and n are defined in the same manner as mentioned above), so that the structure represented by -$L^2$-$\{Si(R^a)_s(R^b)_t(R^c)_u(R^d)_v\}_n$ (wherein $L^2$, $R^a$, $R^b$, $R^c$, $R^d$, s, t, u, v, and n are defined in the same manner as mentioned above) may be introduced into the compound.

In the method of generating a monovalent organic group represented by $R^{22}$—COO—$CH_2CH(OH)$-$L^{23}$- or a monovalent organic group represented by $R^{24}$—O—$CH_2CH(OH)$-$L^{27}$-among the above production methods, the compound represented by H—$\{Si(R^a)_s(R^b)_t(R^c)_u(R^d)_v\}_n$ also reacts with the OH group in the organic group, so that the structure represented by —O—$\{Si(R^a)_s(R^b)_t(R^c)_u(R^d)_v\}_n$ may be introduced into the compound.

Also, when $X^1$ is a group containing a double bond (preferably, an allyl group), a group containing an epoxy group can be introduced into the compound by oxidation using an oxidizing agent such as meta-chloroperoxybenzoic acid, peracetic acid, or hydrogen peroxide or by direct air oxidation using a catalyst to epoxidize the double bond in $X^1$.

Further, when $X^1$ is a group containing a double bond (preferably, an allyl group), a group containing an acryloyl group or a group containing a methacryloyl group can be introduced into the compound by reacting the double bond in $X^1$ and a hydroxyalkyl (meth)acrylate.

The compound of the invention can be used for a variety of applications. Next, examples of the applications of the compound of the invention are described hereinbelow.

The compound of the invention may be used with a polymerizable coating monomer. A composition containing the above compound and a polymerizable coating monomer is also one aspect of the invention (hereinafter, this composition is also referred to as a composition (a)). The composition (a), which has the above structure, can provide a coat which exhibits a high static contact angle against water or n-hexadecane, transparency, and excellent releasability, which is less likely to suffer deposition of fingerprints thereon, and which allows fingerprints deposited thereon to be completely wiped off.

The compound contained in the composition (a) is preferably one in which $X^1$ is a photo-crosslinkable monovalent crosslinkable group.

The polymerizable coating monomer is preferably a monomer containing a carbon-carbon double bond.

The polymerizable coating monomer means a composition containing a compound that may be, but is not limited to, any of monofunctional and/or multifunctional acrylates or methacrylates (hereinafter, acrylates and methacrylates are collectively referred to as "(meth)acrylates"), monofunctional and/or multifunctional urethane (meth)acrylates, and monofunctional and/or multifunctional epoxy (meth)acrylates. The composition to constitute the matrix may be, but is not limited to, a composition that is usually to serve as a hard coating agent or an anti-reflective agent, and examples thereof include hard coating agents containing a multifunctional (meth)acrylate and anti-reflective agents containing a fluorine-containing (meth)acrylate. Examples of commercially available products of the hard coating agent include Beamset 502H, 504H, 505A-6, 550B, 575CB, 577, and 1402 (trade name, Arakawa Chemical Industries, Ltd.), Ebecryl 40 (trade name, Daicel Cytec Co., Ltd.), and HR300 series (trade name, The Yokohama Rubber Co., Ltd.). An example of commercially available products of the anti-reflective agent is Optool AR-110 (trade name, Daikin Industries, Ltd.).

The composition (a) may further contain any of additives such as antioxidants, thickening agents, leveling agents, antifoams, antistatics, antifogging agents, ultraviolet absorbers, pigments, dyes, inorganic fine particles such as silica, fillers such as aluminum paste, talc, glass frit, and metal powder, and polymerization inhibitors such as butylated hydroxytoluene (BHT) and phenothiazine (PTZ).

The composition (a) preferably further contains a solvent. Examples of the solvent include a fluorine-containing organic solvent and a fluorine-free organic solvent.

Examples of the fluorine-containing organic solvent include perfluorohexane, perfluorooctane, perfluorodimethylcyclohexane, perfluorodecalin, perfluoroalkyl ethanol, perfluorobenzene, perfluorotoluene, perfluoroalkyl amine (e.g., Florinert (trade name)), perfluoroalkyl ether, perfluorobutyl tetrahydrofuran, polyfluoroaliphatic hydrocarbon (Asahiklin AC6000 (trade name)), hydrochlorofluorocarbon (e.g., Asahiklin AK-225 (trade name)), hydrofluoroether (e.g., Novec (trade name), HFE-7100 (trade name), HFE-7300 (trade name)), 1,1,2,2,3,3,4-heptafluorocyclopentane, fluorine-containing alcohol, perfluoroalkyl bromide, perfluoroalkyl iodide, perfluoropolyether (e.g., Krytox (trade name), Demnum (trade name), Fomblin (trade name)), 1,3-bistrifluoromethylbenzene, 2-(perfluoroalkyl)ethyl methacrylate, 2-(perfluoroalkyl)ethyl acrylate, perfluoroalkylethylene, Freon 134a, and hexafluoropropene oligomers.

Examples of the fluorine-free organic solvent include acetone, methyl isobutyl ketone, cyclohexanone, propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, dipropylene glycol dimethyl ether pentane, hexane, heptane, octane, dichloromethane, chloroform, carbon tetrachloride, dichloroethane, carbon disulfide, benzene, toluene, xylene, nitrobenzene, diethyl ether, dimethoxyethane, diglyme, triglyme, ethyl acetate, butyl acetate, dimethyl formamide, dimethyl sulfoxide, 2-butanone, acetonitrile, benzonitrile, butanol, 1-propanol, 2-propanol, ethanol, methanol, and diacetone alcohol.

The solvent is preferably methyl isobutyl ketone, propylene glycol monomethyl ether, hexadecane, butyl acetate, acetone, 2-butanone, cyclohexanone, ethyl acetate, diacetone alcohol, or 2-propanol.

These solvents may be used alone or in combination of two or more.

The solvent is preferably used in an amount of 30 to 95 mass % in the composition (a). This amount is more preferably 50 to 90 mass %.

For example, the composition (a) can form an antifouling layer when applied to a substrate. Further, an antifouling layer may be formed by polymerizing the composition applied.

Examples of the substrate include resins (especially, non-fluororesins), metals, and metal oxides.

An example of the metal oxides is glass.

For the substrate which is glass, one or both of $X^1$ and $X^2$ are preferably the crosslinkable groups in order to achieve good adhesiveness between the substrate and the antifouling layer. One or both of $X^1$ and $X^2$ are more preferably monovalent Si-containing groups, and one or both of $X^1$ and $X^2$ are still more preferably silane-containing reactive crosslinkable groups.

The compound of the invention may be used with a curable resin or a curable monomer. A composition containing the above compound and a curable resin or curable monomer is also one aspect of the invention (hereinafter, this composition is also referred to as a composition (b)). The composition (b), which has the above structure, can provide a coat which is less likely to suffer deposition of fingerprints thereon and which allows fingerprints deposited thereon to be completely wiped off.

The curable resin may be either a photo-curable resin or a thermosetting resin, and may be any resin having heat resistance and strength. A photo-curable resin is preferred, and an ultraviolet-curable resin is more preferred.

Examples of the curable resin include acrylic polymers, polycarbonate polymers, polyester polymers, polyamide polymers, polyimide polymers, polyethersulfone polymers, cyclic polyolefin polymers, fluorine-containing polyolefin polymers (e.g., PTFE), and fluorine-containing cyclic amorphous polymers (e.g., Cytop®, Teflon® AF).

Specific examples of the curable resin or monomers constituting the curable resin include alkyl vinyl ethers such as cyclohexyl methyl vinyl ether, isobutyl vinyl ether, cyclohexyl vinyl ether, and ethyl vinyl ether, glycidyl vinyl ether, vinyl acetate, vinyl pivalate, (meth)acrylates such as phenoxyethyl acrylate, benzyl acrylate, stearyl acrylate, lauryl acrylate, 2-ethylhexyl acrylate, allyl acrylate, 1,3-butanediol diacrylate, 1,4-butanediol diacrylate, 1,6-hexanediol diacrylate, trimethylol, propane triacrylate, pentaerythritol triacrylate, dipentaerythritol hexaacrylate, ethoxyethyl acrylate, methoxyethyl acrylate, glycidyl acrylate, tetrahydrofurfuryl acrylate, diethylene glycol diacrylate, neopentyl glycol diacrylate, polyoxyethylene glycol diacrylate, tripropylene glycol diacrylate, 2-hydroxyethyl acrylate, 2-hydroxypropyl acrylate, 4-hydroxybutyl vinyl ether, N,N-diethylaminoethyl acrylate, N,N-dimethylaminoethyl acrylate, N-vinylpyrrolidone, and dimethylaminoethyl methacrylate, silicone-based acrylates, maleic anhydride, vinylene carbonate, linear side chain polyacrylates, cyclic side chain polyacrylates, polynorbornene, polynorbornadiene, polycarbonate, polysulfonamide, and fluorine-containing cyclic amorphous polymers (e.g., Cytop®, Teflon® AF).

The curable monomer may be either a photo-curable monomer or a thermosetting monomer, and is preferably an ultraviolet-curable monomer.

Examples of the curable monomer include (a) urethane (meth)acrylates, (b) epoxy (meth)acrylates, (c) polyester (meth)acrylates, (d) polyether (meth)acrylates, (e) silicone (meth)acrylates, and (f) (meth)acrylate monomers.

Specific examples of the curable monomer include the following.

Examples of the urethane (meth)acrylates (a) include poly((meth)acryloyloxyalkyl)isocyanurates typified by tris(2-hydroxyethyl)isocyanurate diacrylate and tris(2-hydroxyethyl)isocyanurate triacrylate.

The epoxy (meth)acrylates (b) are obtained by adding a (meth)acryloyl group to an epoxy group, typified by those obtained from bisphenol A, bisphenol F, phenol novolac, or an alicyclic compound serving as a starting material.

For the polyester (meth)acrylates (c), the polyester moiety thereof may be constituted by any of polyhydric alcohols such as ethylene glycol, 1,4-butanediol, 1,6-hexanediol, diethylene glycol, trimethylolpropane, dipropylene glycol, polyethylene glycol, polypropylene glycol, pentaerythritol, and dipentaerythritol, and any of polybasic acids such as phthalic acid, adipic acid, maleic acid, trimellitic acid, itaconic acid, succinic acid, terephthalic acid, and alkenylsuccinic acid.

Examples of the polyether (meth)acrylates (d) include polyethylene glycol di(meth)acrylate, polypropylene glycol di(meth)acrylate, and polyethylene glycol-polypropylene glycol di(meth)acrylate.

The silicone (meth)acrylates (e) are those obtained by modifying one or both of the ends of dimethyl polysiloxane having a molecular weight of 1,000 to 10,000 with a (meth)acryloyl group, and examples thereof include the following compounds.

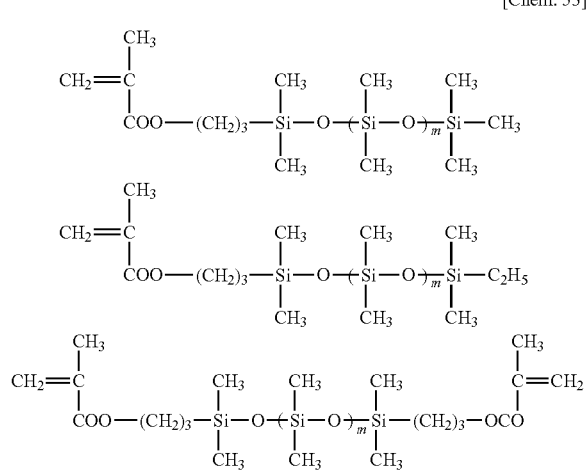

[Chem. 53]

Examples of the (meth)acrylate monomers (f) include methyl (meth)acrylate, ethyl (meth)acrylate, n-propyl (meth)acrylate, isopropyl (meth)acrylate, n-butyl (meth)acrylate, isobutyl (meth)acrylate, sec-butyl (meth)acrylate, t-butyl (meth)acrylate, n-pentyl (meth)acrylate, 3-methylbutyl (meth)acrylate, n-hexyl (meth)acrylate, 2-ethyl-n-hexyl (meth)acrylate, n-octyl (meth)acrylate, cyclohexyl (meth)acrylate, isobornyl (meth)acrylate, benzyl (meth)acrylate, 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth)acrylate, 4-hydroxycyclohexyl (meth)acrylate, neopentyl glycol mono(meth)acrylate, 3-chloro-2-hydroxypropyl (meth)acrylate, (1,1-dimethyl-3-oxobutyl) (meth)acrylate, 2-acetoacetoxyethyl (meth)acrylate, 2-methoxyethyl (meth)acrylate, 2-ethoxyethyl (meth) acrylate, neopentyl glycol mono(meth)acrylate, 3-chloro-2-hydroxypropyl (meth)acrylate, glycerol mono(meth) acrylate, ethylene glycol diacrylate, propylene glycol diacrylate, 1,6-hexanediol diacrylate, 1,9-nonanediol diacrylate, 1,10-decanediol diacrylate, trimethylol propane triacrylate, and pentaerythritol tetraacrylate.

Preferred commercially available products of the curable resin and the curable monomer are as follows.

Examples of commercially available products of the curable resin include: silicone resins such as PAK-01 and PAK-02 (Toyo Gosei Co., Ltd.); nanoimprint resins such as NIF series (Asahi Glass Co., Ltd.); nanoimprint resins such as OCNL series (Tokyo Ohka Kogyo Co., Ltd.) and NIAC 2310 (Daicel Chemical Industries, Co., Ltd.); epoxy acrylate resins such as EH-1001, ES-4004, EX-C101, EX-C106, EX-C300, EX-C501, EX-0202, EX-0205, and EX-5000 (Kyoeisha Chemical Co., Ltd.); and hexamethylene diisocyanate-based polyisocyanates such as Sumidur N-75, Sumidur N3200, Sumidur HT, Sumidur N3300, and Sumidur N3500 (Sumitomo Bayer Urethane Co., Ltd.).

Examples of commercially available products of silicone acrylate resins among the curable monomers include: Silaplane FM-0611, Silaplane FM-0621, and Silaplane FM-0625; bi-terminal-type (meth)acrylate resins such as Silaplane FM-7711, Silaplane FM-7721, and Silaplane FM-7725; Silaplane FM-0411, Silaplane FM-0421, Silaplane FM-0428, Silaplane FM-DA11, Silaplane FM-DA21, and Silaplane DA25; mono-terminal-type (meth)acrylate resins such as Silaplane FM-0711, Silaplane FM-0721, Silaplane FM-0725, Silaplane TM-0701, and Silaplane TM-070IT (JCN Co., Ltd.).

Examples of commercially available products of polyfunctional acrylates include A-9300, A-9300-1CL, A-GLY-9E, A-GLY-20E, A-TMM-3, A-TMM-3L, A-TMM-3LM-N, A-TMPT, and A-TMMT (Shin-Nakamura Chemical Co., Ltd.).

An example of preferred commercially available products of polyfunctional methacrylates is TMPT (Shin-Nakamura Chemical Co., Ltd.).

Examples of commercially available products of alkoxysilane group-containing (meth)acrylates include 3-(meth) acryloyloxypropyltrichlorosilane, 3-(meth)acryloyloxypropyltrimethoxysilane, 3-(meth) acryloyloxypropyltriethoxysilane, 3-(meth) acryloyloxypropyltriisopropoxysilane, (also referred to as (triisopropoxysilyl)propyl methacrylate (abbreviation: TISMA) and (triisopropoxysilyl)propyl acrylate), 3-(meth) acryloxyisobutyltrichlorosilane, 3-(meth)acryloxyisobutyltriethoxysilane, 3-(meth)acryloxyisobutyltriisopropoxysilane, and 3-(meth)acryloxyisobutyltrimethoxysilane.

The composition (b) may also preferably contain a crosslinking catalyst. Examples of the crosslinking catalyst include a radical polymerization initiator and an acid generator.

The radical polymerization initiator is a compound that generates a radical by heat or light, and examples thereof include a radical thermal polymerization initiator and a radical photo-polymerization initiator. In the invention, a radical photo-polymerization initiator is preferred.

Examples of the radical thermal polymerization initiator include: peroxide compounds, including diacyl peroxides such as benzoyl peroxide and lauroyl peroxide, dialkyl peroxides such as dicumyl peroxide and di-t-butyl peroxide, peroxy carbonates such as diisopropyl peroxydicarbonate and bis(4-t-butylcyclohexyl)peroxydicarbonate, and alkyl peresters such as t-butyl peroxyoctoate and t-butyl peroxybenzoate; and radical-generating azo compounds such as azobisisobutyronitrile.

Examples of the radical photo-polymerization initiator include: -diketones such as benzyl and diacetyl; acyloins such as benzoin; acyloin ethers such as benzoin methyl ether, benzoin ethyl ether, and benzoin isopropyl ether; thioxanthones such as thioxanthone, 2,4-diethyl thioxanthone, and thioxanthone-4-sulfonic acid; benzophenones such as benzophenone, 4,4'-bis(dimethylamino)benzophenone, and 4,4'-bis(diethylamino)benzophenone; acetophenones such as acetophenone, 2-(4-toluenesulfonyloxy)-2-phenylacetophenone, p-dimethylaminoacetophenone, 2,2'-dimethoxy-2-phenylacetophenone, p-methoxyacetophenone, 2-methyl[4-(methylthio)phenyl]-2-morpholino-1-propanone, and 2-benzyl-2-dimethyl-amino-1-(4-morpholinophenyl)-butan-1-one; quinones such as anthraquinone and 1,4-naphthoquinone; aminobenzoic acids such as ethyl 2-dimethylaminobenzoate, ethyl 4-dimethylaminobenzoate, (n-butoxy)ethyl 4-dimethylaminobenzoate, isoamyl 4-dimethylaminobenzoate, and 2-ethylhexyl 4-dimethylaminobenzoate; halogen compounds such as phenacyl chloride and trihalomethyl phenyl sulfone; acyl phosphine oxides; and peroxides such as di-t-butyl peroxide.

Examples of commercially available products of the radical photo-polymerization initiator include:

Irgacure 651: 2,2-dimethoxy-1,2-diphenylethan-1-one,
Irgacure 184: 1-hydroxy-cyclohexyl-phenyl-ketone,
Irgacure 2959: 1-[4-(2-hydroxyethoxy)-phenyl]-2-hydroxy-2-methyl-1-propan-1-one,
Irgacure 127: 2-hydroxy-1-{4-[4-(2-hydroxy-2-methyl-propionyl)-benzyl]-phenyl}-2-methyl-propan-1-one,
Irgacure 907: 2-methyl-1-(4-methylthiophenyl)-2-morpholinopropan-1-one,
Irgacure 369: 2-benzyl-2-dimethylamino-1-(4-morpholinophenyl)-butanone-1,
Irgacure 379: 2-(dimethylamino)-2-[(4-methylphenyl)methyl]-1-[4-(4-morpholinyl)phenyl]-1-butanone,
Irgacure 819: bis(2,4,6-trimethylbenzoyl)-phenylphosphine oxide,
Irgacure 784: bis(η5-2,4-cyclopentadien-1-yl)-bis(2,6-difluoro-3-(1H-pyrrol-1-yl)-phenyl)titanium,
Irgacure OXE01: 1,2-octanedione, 1-[4-(phenylthio)-], 2-(O-benzoyloxime),
Irgacure OXE02: ethanone, 1-[9-ethyl-6-(2-methylbenzoyl)-9H-carbazol-3-yl]-, 1-(O-acetyloxime),
Irgacure 261, Irgacure 369, Irgacure 500,
Darocur 1173: 2-hydroxy-2-methyl-1-phenyl-propan-1-one,
Darocur TPO: 2,4,6-trimethylbenzoyl-diphenyl-phosphine oxide,
Darocur 1116, Darocur 2959, Darocur 1664, Darocur 4043,
Irgacure 754 oxy-phenylacetic acid: Mixture of oxy-phenylacetic acid 2-[2-oxo-phenylacetoxyethoxy]ethyl ester and 2-(2-hydroxyethoxy)ethyl ester,
Irgacure 500: Mixture of Irgacure 184 and benzophenone (1:1),
Irgacure 1300: Mixture of Irgacure 369 and Irgacure 651 (3:7),
Irgacure 1800: Mixture of CGI403 and Irgacure 184 (1:3),
Irgacure 1870: Mixture of CGI403 and Irgacure 184 (7:3), and
Darocur 4265: Mixture of Darocur TPO and Darocur 1173 (1:1).

Irgacures are produced by BASF SE and Darocurs are produced by Merck Japan.

A radical photo-polymerization initiator serving as the crosslinking catalyst may be used in combination with a sensitizer such as diethylthioxanthone or isopropylthioxanthone and with a polymerization accelerator such as Darocur EDB (ethyl-4-dimethylaminobenzoate) and Darocur EHA (2-ethylhexyl-4-dimethylaminobenzoate).

The amount of the sensitizer when used is preferably 0.1 to 5 parts by mass relative to 100 parts by mass of the curable resin or the curable monomer. The amount thereof is more preferably 0.1 to 2 parts by mass.

The amount of the polymerization accelerator when used is preferably 0.1 to 5 parts by mass relative to 100 parts by mass of the curable resin or the curable monomer. The amount thereof is more preferably 0.1 to 2 parts by mass.

The acid generator is a material capable of generating an acid by application of heat or light, and examples thereof include a thermal acid generator and a photo-acid generator. In the invention, a photo-acid generator is preferred.

Examples of the thermal acid generator include benzoin tosylate, nitrobenzyl tosylate (especially, 4-nitrobenzyl tosylate), and alkyl esters of other organic sulfonic acids.

The photo-acid generator is composed of a chromophore that absorbs light and an acid precursor that is to be converted into an acid after decomposition. Application of light of a specific wavelength excites a photo-acid generator having such a structure, generating an acid from the acid precursor moiety.

Examples of the photo-acid generator include salts such as diazonium salts, phosphonium salts, sulfonium salts, iodonium salts, $CF_3SO_3$, $p-CH_3PhSO_3$, and $p-NO_3PhSO_3$ (wherein Ph is a phenyl group), organohalogen compounds, orthoquinone-diazide sulfonyl chloride, and sulfonic acid esters. Examples of the photo-acid generator also include 2-halomethyl-5-vinyl-1,3,4-oxadiazole compounds, 2-trihalomethyl-5-aryl-1,3,4-oxadiazole compounds, and 2-trihalomethyl-5-hydroxyphenyl-1,3,4-oxadiazole compounds.

The organohalogen compounds are compounds that generate a hydrohalic acid (e.g., hydrogen chloride).

Examples of commercially available products of the photo-acid generator include the following:

products of Wako Pure Chemical Industries, Ltd., such as WPAG-145 (bis(cyclohexylsulfonyl)diazomethane), WPAG-170 (bis(t-butylsulfonyl)diazomethane), WPAG-199 (bis(p-toluenesulfonyl)diazomethane), WPAG-281 (triphenylsulfonium trifluoromethanesulfonate), WPAG-336 (diphenyl-4-methylphenylsulfonium trifluoromethanesulfonate), and WPAG-367 (diphenyl-2,4,6-trimethylphenylsulfonium p-toluenesulfonate); products of Ciba Specialty Chemicals Inc., such as Irgacure PAG103 ((5-propylsulfonyloxyimino-5H-thiophen-2-ylidene)-(2-methylphenyl)acetonitrile), Irgacure PAG108 ((5-octylsulfonyloxyimino-5H-thiophen-2-ylidene)-(2-methylphenyl)acetonitrile)), Irgacure PAG121 ((5-p-toluenesulfonyloxyimino-5H-thiophen-2-ylidene)-(2-methylphenyl)acetonitrile), Irgacure PAG203, and CGI725; and products of Sanwa Chemical Co., such as TFE-triazine (2-[2-(furan-2-yl)ethenyl]-4,6-bis(trichloromethyl)-s-triazine), TME-triazine (2-[2-(5-methylfuran-2-yl)ethenyl]-4,6-bis(trichloromethyl)-s-triazine), MP-triazine (2-(methoxyphenyl)-4,6-bis(trichloromethyl)-s-triazine), and dimethoxy [2-[2-(3,4-dimethoxyphenyl)ethenyl]-4,6-bis(trichloromethyl)-s-triazine].

The amount of the crosslinking catalyst is preferably 0.1 to 10 parts by mass relative to 100 parts by mass of the curable resin or the curable monomer. The crosslinking catalyst in an amount within this range can provide a sufficiently cured product. The amount of the crosslinking catalyst is more preferably 0.3 to 5 parts by mass, still more preferably 0.5 to 2 parts by mass.

When an acid generator is used as the crosslinking catalyst, an acid scavenger may be added as appropriate to control diffusion of the acid generated from the acid generator.

The acid scavenger is preferably, but is not limited to, a basic compound such as amines (particularly, organic amines), basic ammonium salts, and basic sulfonium salts. In order to achieve excellent imaging performance, organic amines are more preferred among these acid scavengers.

Specific examples of the acid scavenger include 1,5-diazabicyclo[4.3.0]-5-nonene, 1,8-diazabicyclo[5.4.0]-7-undecene, 1,4-diazabicyclo[2.2.2]octane, 4-dimethylaminopyridine, 1-naphthylamine, piperidine, hexamethylenetetramine, imidazoles, hydroxypyridines, pyridines, 4,4'-diaminodiphenyl ether, pyridinium p-toluenesulfonate, 2,4,6-trimethylpyridinium p-toluenesulfonate, tetramethylammonium p-toluenesulfonate, tetrabutylammonium lactate, triethylamine, and tributylamine. Preferred among these are organic amines such as 1,5-diazabicyclo[4.3.0]-5-nonene, 1,8-diazabicyclo[5.4.0]-7-undecene, 1,4-diazabicyclo[2.2.2]octane, 4-dimethylaminopyridine, 1-naphthylamine, piperidine, hexamethylenetetramine, imidazoles, hydroxypyridines, pyridines, 4,4'-diaminodiphenyl ether, triethylamine, and tributylamine.

The amount of the acid scavenger is preferably 20 parts by mass or less, more preferably 0.1 to 10 parts by mass, still more preferably 0.5 to 5 parts by mass, relative to 100 parts by mass of the acid generator.

The composition (b) may contain a solvent. Examples of the solvent include water-soluble organic solvents, organic solvents (especially, oil-soluble organic solvents) and water.

Examples of the water-soluble organic solvents include acetone, methyl ethyl ketone, methyl amyl ketone, ethyl acetate, propylene glycol, propylene glycol monomethyl ether, propylene glycol monomethyl ether acetate (PGMEA), dipropylene glycol, dipropylene glycol monomethyl ether, dipropylene glycol dimethyl ether, dipropylene glycol monomethyl ether acetate, dipropylene glycol diacetate, tripropylene glycol, 3-methoxybutyl acetate (MBA), 1,3-butylene glycol diacetate, cyclohexanol acetate, dimethyl formamide, dimethyl sulfoxide, methyl cellosolve, cellosolve acetate, butyl cellosolve, butyl carbitol, carbitol acetate, ethyl lactate, isopropyl alcohol, methanol, and ethanol.

Examples of the organic solvents include chloroform, HFC141b, HCHC225, hydrofluoroether, pentane, hexane, heptane, octane, cyclohexane, benzene, toluene, xylene, petroleum ether, tetrahydrofuran, 1,4-dioxane, methyl isobutyl ketone, butyl acetate, 1,1,2,2-tetrachloroethane, 1,1,1-trichloroethane, trichloroethylene, perchloroethylene, tetrachlorodifluoroethane, and trichlorotrifluoroethane.

These solvents may be used alone or in combination of two or more.

In order to achieve good solubility of the components contained in a resist composition and good safety, the solvent is particularly preferably PGMEA or MBA.

The solvent is preferably used in an amount of 30 to 95 mass % in the composition (b). This amount is more preferably 50 to 90 mass %.

For example, the composition (b) can form a resist film when applied to a substrate. Examples of a material of the substrate include silicones, synthetic resins, glass, metals, and ceramics.

Examples of the synthetic resins include cellulose resins such as triacetyl cellulose (TAC), polyolefins such as polyethylene, polypropylene, ethylene-propylene copolymers, and ethylene-vinyl acetate copolymers (EVA), cyclic polyolefins, modified polyolefins, polyvinyl chloride, polyvinylidene chloride, polystyrene, polyamide, polyimide, polyamide-imide, polycarbonate, poly-(4-methyl pentene-1), ionomers, acrylic resin, polymethyl methacrylate, acryl-styrene copolymers (AS resin), butadiene-styrene copolymers, ethylene-vinyl alcohol copolymers (EVOH), polyesters such as polyethylene terephthalate (PET), polybutylene terephthalate (PBT), and polycyclohexane terephthalate (PCT), polyether, polyether ketone (PEK), polyether ether ketone (PEEK), polyetherimide, polyacetal (POM), polyphenylene oxide, modified polyphenylene oxide, polyarylate, aromatic polyester (liquid crystal polymers), polytetrafluoroethylene, polyvinylidene fluoride, other fluororesins, styrene-, polyolefin-, polyvinyl chloride-, polyurethane-, fluororubber-, or chlorinated polyethylene-based thermoplastic elastomers, epoxy resin, phenol resin, urea resin, melamine resin, unsaturated polyester, silicone resin, and polyurethane, and copolymers, blends, and polymer alloys mainly formed from these polymers. One of these may be used or two or more of these may be used in combination (for example, in the form of a laminate of two or more layers).

The resist film can be used in nanoimprinting. For example, a resist cured product with a pattern transferred thereon may be produced by a production method including: pressing a mold with a fine pattern formed on the surface thereof to the resist film to transfer the fine pattern; curing the resist film with the transferred pattern formed thereon to provide a resist cured product with the transferred pattern; and releasing the resist cured product from the mold.

The compound of the invention can be used with a solvent. A composition containing the above compound and a solvent is also one aspect of the invention (hereinafter, also referred to as a composition (c)).

The composition (c) preferably contains the compound at a concentration of 0.001 to 1 mass %, more preferably 0.005 to 0.5 mass %, still more preferably 0.01 to 0.2 mass %.

The solvent is preferably a fluorosolvent. Examples of inert fluorosolvents include perfluorohexane, perfluoromethyl cyclohexane, perfluoro-1,3-dimethyl cyclohexane, and dichloropentafluoropropane (HCFC-225).

The composition (c) may also preferably contain a fluorine-containing oil. The fluorine-containing oil is more preferably a compound represented by the following formula:

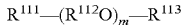

wherein $R^{111}$ and $R^{113}$ are each individually F, a C1-C16 alkyl group, a C1-C16 fluorinated alkyl group, or —$R^{114}$—$X^{111}$ (wherein $R^{114}$ is a single bond or a C1-C16 alkylene group; and $X^{111}$ is —$NH_2$, —OH, —COOH, —CH=$CH_2$, —$OCH_2CH$=$CH_2$, a halogen, phosphoric acid, a phosphoric acid ester, a carboxylic acid ester, thiol, thioether, an alkyl ether (optionally substituted with fluorine), an aryl, an aryl ether, or an amide); $R^{112}$ is a C1-C4 fluorinated alkylene group; and m is an integer of 2 or greater.

$R^{111}$ and $R^{113}$ are preferably each individually F, a C1-C3 alkyl group, a C1-C3 fluorinated alkyl group, or —$R^{114}$—$X^{111}$ (wherein $R^{114}$ and $X^{111}$ are defined in the same manner as mentioned above), more preferably F, a C1-C3 perfluorinated alkyl group, or —$R^{114}$—$X^{111}$ (wherein $R^{114}$ is a single bond or a C1-C3 alkylene group; and $X^{111}$ is —OH or —$OCH_2CH$=$CH_2$).

In the formula, m is preferably an integer of 300 or smaller, more preferably an integer of 100 or smaller.

$R^{112}$ is preferably a C1-C4 perfluorinated alkylene group. Examples of —$R^{112}$O— include:

those represented by the formula:

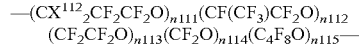

wherein n111, n112, n113, n114, and n115 are each individually an integer of 0 or 1 or greater; $X^{112}$ is H, F, or Cl; and the repeating units may be present in any order; and those represented by the formula:

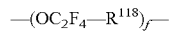

wherein $R^{118}$ is a group selected from $OC_2F_4$, $OC_3F_6$, and $OC_4F_8$; and f is an integer of 2 to 100.

In the formula, n111 to n115 are each preferably an integer of 0 to 200. The sum of n111 to n115 is preferably 1 or greater, more preferably 5 to 300, still more preferably 10 to 200, particularly preferably 10 to 100.

$R^{118}$ is a group selected from $OC_2F_4$, $OC_3F_6$, and $OC_4F_8$, or any combination of two or three groups individually selected from these groups. Examples of the combination of two or three groups individually selected from $OC_2F_4$, $OC_3F_6$, and $OC_4F_8$ include, but are not limited to, $-OC_2F_4OC_3F_6-$, $-OC_2F_4OC_4F_8-$, $-OC_3F_6OC_2F_4-$, $-OC_3F_6OC_3F_6-$, $-OC_3F_6OC_4F_8-$, $-OC_4F_8OC_4F_8-$, $-OC_4F_8OC_3F_6-$, $-OC_4F_8OC_2F_4-$, $-OC_2F_4OC_2F_4OC_3F_6-$, $-OC_2F_4OC_2F_4OC_4F_8-$, $-OC_2F_4OC_3F_6OC_2F_4-$, $-OC_2F_4OC_3F_6OC_3F_6-$, $-OC_2F_4OC_4F_8OC_2F_4-$, $-OC_3F_6OC_2F_4OC_2F_4-$, $-OC_3F_6OC_2F_4OC_3F_6-$, $-OC_3F_6OC_3F_6OC_2F_4-$, and $-OC_4F_8OC_2F_4OC_2F_4-$. In the formula, f is an integer of 2 to 100, preferably an integer of 2 to 50. In the formula, $OC_2F_4$, $OC_3F_6$, and $OC_4F_8$ each may be linear or branched, and is preferably linear. In this embodiment, the formula: $-(OC_2F_4-R^{118})_f-$ is preferably $-(OC_2F_4-OC_3F_6)_f-$ or $-(OC_2F_4-OC_4F_8)_f-$.

The fluoropolyether preferably has a weight average molecular weight of 500 to 100000, more preferably 50000 or less, still more preferably 10000 or less, particularly preferably 6000 or less. The weight average molecular weight can be determined by gel permeation chromatography (GPC).

Examples of commercially available products of the fluoropolyether include Demnum (Daikin Industries, Ltd.), Fomblin (Solvay Specialty Polymers Japan K. K.), Barrierta (NOK Kluber Co., Ltd.), and Krytox (DuPont).

The composition (c) can form a release layer on a substrate. The release layer may be formed by, for example, a method of immersing the substrate into the composition (c); a method of exposing the substrate to the vapor of the composition (c), thereby vapor-depositing the composition (c) on the substrate; a method of printing the composition (c) on the substrate; or a method of inkjet-applying the composition (c) to the substrate. The immersion, deposition, printing, or application may be followed by drying. The substrate may be a mold with an uneven pattern formed thereon, and the mold with a release layer formed thereon can be used in nanoimprinting.

In the case where one or both of $X^1$ and $X^2$ are the crosslinkable groups, the release layer can be firmly bonded to the substrate.

In the case where both $X^1$ and $X^2$ are groups other than the crosslinkable group, the release layer can be easily removed from the substrate. For example, when the release layer is formed on the mold and used in nanoimprinting, the compound can be attached to a transfer target to give releasability.

Examples of the substrate include metals, metal oxides, quartz, polymeric resins such as silicones, semiconductors, insulators, and composites thereof.

The invention also relates to an antifouling agent containing the above compound or the above composition.

The antifouling agent can be applied to substrates such as resins (especially non-fluororesins), metals, and glass, for use.

The antifouling agent can be used for a variety of articles (especially, optical materials) requiring surface antifouling performance and swellability. Examples of the articles include front screen protectors, antireflection films, polarizers, and antiglare films for displays such as PDP and LCD, devices such as mobile phones and personal digital assistants, touchscreen sheets, optical discs such as DVDs, CD-Rs, and MOs, spectacle lenses, and optical fibers.

Optical materials of articles such as optical discs preferably have a surface coated with a film formed from a compound containing a carbon-carbon double bond-containing composition or a polymer of a carbon-carbon double bond-containing composition in which the amount of perfluoropolyether (PFPE) is 0.01 to 10 wt % in the carbon-carbon double bond-containing composition or in the polymer of a carbon-carbon double bond-containing monomer. PFPE added in an amount of 0.01 to 10 wt % can provide characteristic physical properties (e.g., antifouling performance), a high surface hardness, and a high transmittance.

The invention also relates to a release agent containing the above compound or the above composition.

The release agent can form a release layer on a substrate. The release layer may be formed by, for example, a method of immersing the substrate into the release agent; a method of exposing the substrate to the vapor of the release agent, thereby vapor-depositing the release agent on the substrate; a method of printing the composition on the substrate; or a method of inkjet-applying the composition to the substrate. The immersion, deposition, printing, or application may be followed by drying. The substrate may be a mold with an uneven pattern formed thereon, and the mold with a release layer formed thereon can be used in nanoimprinting.

Examples of the substrate include metals, metal oxides, quartz, polymeric resins such as silicones, semiconductors, insulators, and composites thereof.

EXAMPLES

The invention is described with reference to, but is not limited to, examples. In the following examples, all the formulae show the respective average compositions, and the repeating units constituting the perfluoropolyether (e.g., $-CF_2CF_2CF_2O-$, $-CF_2CF_2O-$, $-CF_2O-$) may be present in any order.

The parameters in the examples were determined by the following methods.

(Static Contact Angle)

The static contact angle was determined by the following method using a fully automatic contact angle meter Drop-Master 700 (Kyowa Interface Science Co., Ltd.).

<Measurement of Static Contact Angle>

The static contact angle was determined by dropping 2 μL of water or n-hexadecane from a micro syringe onto a substrate placed horizontally and taking a still image with a video microscope one second after the dropping.

Example 1: Method of Producing Perfluoropolyether (PFPE)-Containing Compound (A)

In a reactor, 34 g of $CF_3CF_2CF_2O-(CF_2CF_2CF_2O)_{11}-CF_2CF_2CH_2OH$ and 6 g of 1,3-diallyl-5-(2-chloroethyl) isocyanurate were dissolved in a solvent mixture of m-hexafluoroxylene and diethylene glycol dimethyl ether. Then, 20 g of a 20 wt % aqueous solution of potassium hydroxide and 4 g of tetrabutyl ammonium bromide were added thereto and the components were heated under stirring. The completion of the reaction was confirmed by $^{19}F$-NMR and $^1H$-NMR. The reaction solution was concentrated and extracted, whereby a PFPE-containing compound (A) was obtained.

PFPE-Containing Compound (A):

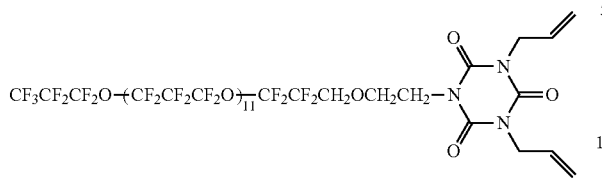

Example 2: Method of Producing Perfluoropolyether (PFPE)-Containing Compound (B)

A PFPE-containing compound (B) was obtained in the same manner as in Example 1 except that 6 g of 1,3-diallyl-5-(2-chloroethyl)isocyanurate in Example 1 was changed to 6.2 g of 1,3-diallyl-5-glycidyl isocyanurate.

PFPE-Containing Compound (B):

 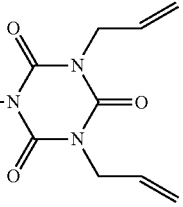

Example 3: Method of Producing Perfluoropolyether (PFPE)-Containing Compound (C)

First, 2.0 g of 1,3-diallyl isocyanurate was dissolved in a solvent mixture of m-hexafluoroxylene and dimethyl formamide. Then, 1.0 g of potassium carbonate was added thereto and the components were heated under stirring. Further, 4.0 g of $CF_3CF_2CF_2O$—$(CF_2CF_2CF_2O)_{23}$—$CF_2CF_2CH_2$-trifluoromethane sulfonate dissolved in m-hexafluoroxylene was added thereto and the heating under stirring was continued. The completion of the reaction was confirmed by $^{19}F$-NMR and $^{1}H$-NMR. Pure water was added to the reaction solution and the resulting liquid was separated, whereby a PFPE-containing compound (C) was obtained.

PFPE-Containing Compound (C):

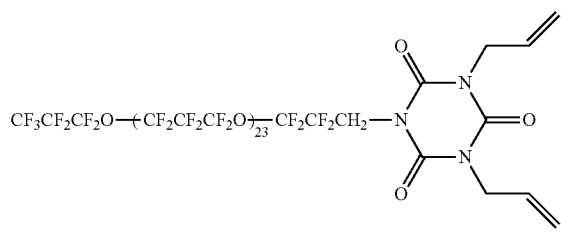

Example 4: Method of Producing Perfluoropolyether (PFPE)-Containing Compound (D)

A PFPE-containing compound (D) was obtained in the same manner as in Example 3 except that 4.0 g of $CF_3CF_2CF_2O$—$(CF_2CF_2CF_2O)_{23}$—$CF_2CF_2CH_2$-trifluoromethane sulfonate in Example 3 was changed to 8.0 g of $CF_3CF_2CF_2O$—$(CF_2CF_2CF_2O)_{11}$—$CF_2CF_2CH_2Cl$.

Example 5: Method of Producing Perfluoropolyether (PFPE)-Containing Compound (E)

A reactor was charged with 30 ml of m-hexafluoroxylene and 11.1 g of m-chloroperoxybenzoic acid, and the components were warmed up to 60° C. under stirring. Then, 10 g of the PFPE-containing compound (D) dissolved in 10 ml of m-hexafluoroxylene was added dropwise thereto and the components were stirred at 60° C. The completion of the reaction was confirmed by $^{19}F$-NMR and $^{1}H$-NMR. The temperature of the reaction solution was returned to room temperature. A white solid precipitate was filtered off and the filtrate was concentrated to 20 ml. The white solid precipitate was dissolved in 10 ml of diethyl ether, and the oil phase in the lower layer was collected. The residual solvent was evaporated from the oil phase, whereby a PFPE-containing compound (E) was obtained.

PFPE-Containing Compound (E):

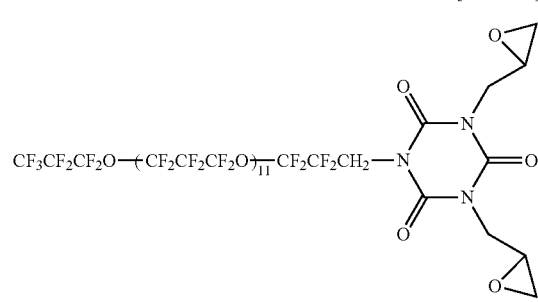

Example 6: Method of Producing Perfluoropolyether (PFPE)-Containing Compound (F)

First, 2.0 g of 2-hydroxyethyl acrylate was dissolved in a solvent mixture of m-hexafluoroxylene and dimethyl formamide. Then, 1.0 g of potassium carbonate was added thereto and the components were warmed up to 40° C. and stirred.

To this reaction solution was added 4.0 g of the PFPE-containing compound (E) dissolved in m-hexafluoroxylene, and the heating under stirring was continued. The completion of the reaction was confirmed by $^{19}$F-NMR and $^{1}$H-NMR. Pure water was added to the reaction solution and the resulting liquid was separated, whereby a PFPE-containing compound (F) was obtained.

PFPE-Containing Compound (F):

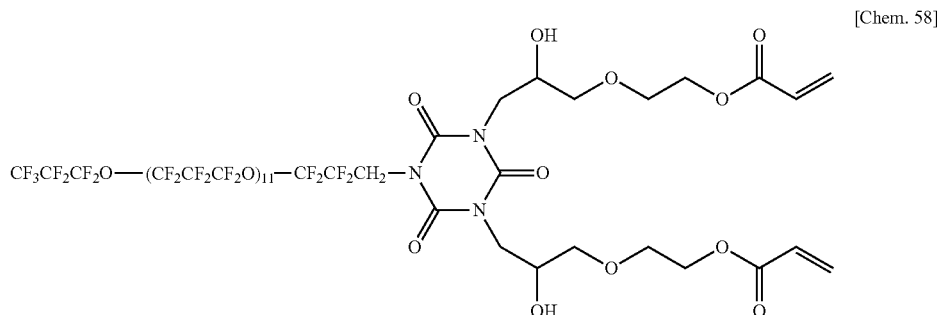

[Chem. 58]

<Evaluation of Characteristics of Cured Film>

To 6.0 g of Beamset 575CB (Arakawa Chemical Industries, Ltd.) were added 120 mg of Irgacure 907 (BASF SE) serving as a photo-polymerization initiator and the PFPE-containing compound (A), (B), (D), (E), or (F) in an amount of 2 mass % of the whole mass. The components were stirred using a rotary mixer under shade for a whole day and night. Thereby, PFPE-containing hard coat materials 1 to 5 were obtained. Another hard coat material was obtained in the same manner, except that the PFPE-containing compound (A), (B), (D), (E), or (F) was changed to DAC-HP (Daikin Industries, Ltd.), which was used in Comparative Example 1. Still another hard coat material consisting only of Beamset 575CB (Arakawa Chemical Industries, Ltd.) and free from a PFPE-containing compound was used in Comparative Example 2.

Each hard coat material (10 μL) was placed on a glass slide, and a uniform coat was formed with a bar coater. The coat was irradiated with light beams including 365-nm UV light at an intensity of 500 mJ/cm$^2$ in a nitrogen atmosphere, so that the hard coat material was cured. Thereby, a cured film was obtained. The static contact angle of each cured film was determined.

(Appearance)

The appearance of each cured film was visually observed. The evaluation was based on the following criteria.
Good: Transparent
Poor: Cloudy (Releasability)

The releasability of each cured film was evaluated by a tape peeling test. The evaluation was based on the following criteria.

Good: The tape was easily peeled off or did not adhere.
Poor: The adhesive layer of tape adhered.

(Fingerprint Deposition Property)

A finger was pushed against the cured film, and the ease of depositing a fingerprint was visually evaluated. The evaluation was based on the following criteria.

Good: A fingerprint was less likely to deposit on the cured film, or even when a fingerprint was deposited, it was difficult to see.
Poor: A fingerprint was clearly deposited on the cured film.

(Ease of Wiping Off Fingerprint)

After the above fingerprint deposition test, the fingerprint deposited was wiped off five times in a reciprocative manner with KimWipes (trade name, Jujo Kimberly Co., Ltd.). The ease of wiping off the fingerprint deposited was visually observed. The evaluation was based on the following criteria.

Good: The fingerprint was completely wiped off.
Poor: The mark of wiping off the fingerprint spread and was difficult to remove.

The results of the respective evaluations are shown in Table 1.

TABLE 1

| Hard coat material before curing | Static contact angle (degree) | | Appearance | Releasability | Fingerprint deposition performance | Ease of wiping off fingerprint |
|---|---|---|---|---|---|---|
| | Water | n-Hexadecane | | | | |
| PFPE-containing hard coat material 1 | 109 | 65 | Good | Good | Good | Good |
| PFPE-containing hard coat material 2 | 107 | 67 | Good | Good | Good | Good |
| PFPE-containing hard coat material 3 | 110 | 66 | Good | Good | Good | Good |
| PFPE-containing hard coat material 4 | 110 | 68 | Good | Good | Good | Good |
| PFPE-containing hard coat material 5 | 111 | 67 | Good | Good | Good | Good |
| Comparative Example 1 | 108 | 65 | Poor | Good | Good | Good |
| Comparative Example 2 | 51 | 19 | Good | Poor | Poor | Poor |

Example 7: Method of Producing Perfluoropolyether (PFPE)-Containing Compound (G)

First, 10.1 g of the PFPE-containing compound (C), 40 g of m-hexafluoroxylene, 0.04 g of triacetoxymethylsilane, and 1.93 g of trichlorosilane were stirred at 10° C. for 30 minutes. Then, 0.115 ml of a xylene solution containing 2% Pt complex of 1,3-divinyl-1,1,3,3-tetramethyldisiloxane was added thereto and the components were heated and stirred for four hours. The volatile component was evaporated under reduced pressure. A solution mixture of 0.23 g of methanol and 6.1 g of trimethyl orthoformate was added and the components were heated and stirred for three hours. The resulting product was purified, whereby 9.9 g of the following PFPE-containing compound (G) containing trimethoxysilyl groups at ends was obtained.

PFPE-Containing Compound (G):

[Chem. 59]

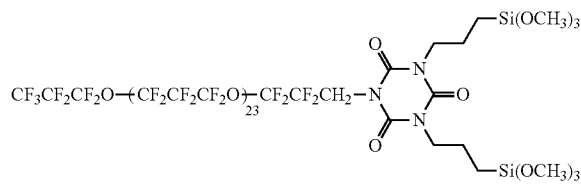

Example 8: Method of Producing Perfluoropolyether (PFPE)-Containing Compound (H)

First, 10.0 g of the PFPE-containing compound (A), 30 g of m-hexafluoroxylene, 0.06 g of triacetoxymethylsilane, and 3.85 g of trichlorosilane were stirred at 10° C. for 30 minutes. Then, 0.210 ml of a xylene solution containing 2% Pt complex of 1,3-divinyl-1,1,3,3-tetramethyldisiloxane was added thereto and the components were heated and stirred for three hours. The volatile component was evaporated under reduced pressure. A solution mixture of 0.31 g of methanol and 7.5 g of trimethyl orthoformate was added and the components were heated and stirred for three hours. The resulting product was purified, whereby 9.8 g of the following PFPE-containing compound (H) containing trimethoxysilyl groups at ends was obtained.

PFPE-Containing Compound (H):

[Chem. 60]

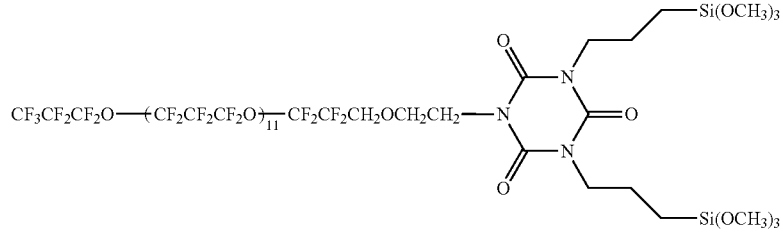

Example 9: Method of Producing Perfluoropolyether (PFPE)-Containing Compound (I)

A PFPE-containing compound (I) was obtained in the same manner as in Example 8, except that the PFPE-containing compound (A) in Example 8 was changed to the PFPE-containing compound (B) and the amount of trichlorosilane was changed to 4.75 g.

PFPE-Containing Compound (I):

[Chem. 61]

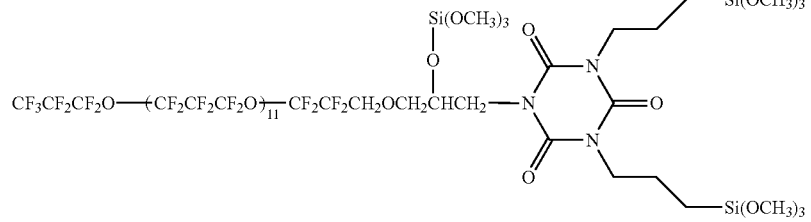

Example 10: Method of Producing Perfluoropolyether (PFPE)-Containing Compound (J)

First, 10.2 g of the PFPE-containing compound (D), 30 g of m-hexafluoroxylene, 0.06 g of triacetoxymethylsilane, and 3.85 g of trichlorosilane were stirred at 10° C. for 30 minutes. Then, 0.220 ml of a xylene solution containing 2% Pt complex of 1,3-divinyl-1,1,3,3-tetramethyldisiloxane was added thereto and the components were heated and stirred for four hours. The volatile component was evaporated under reduced pressure. A solution mixture of 0.30 g of methanol and 7.5 g of trimethyl orthoformate was added and the components were heated and stirred for three hours. The resulting product was purified, whereby 10.0 g of the following PFPE-containing compound (J) containing trimethoxysilyl groups at ends was obtained.

PFPE-Containing Compound (J):

[Chem. 62]

$CF_3CF_2CF_2O\!-\!(CF_2CF_2CF_2O)_{11}\!-\!CF_2CF_2CH_2\!-\!$ [triazine ring with two $-CH_2CH_2CH_2Si(OCH_3)_3$ groups]

Example 11: Method of Producing Perfluoropolyether (PFPE)-Containing Compound (L)

In a reactor, 33 g of $CF_3O\!-\!(CF_2CF_2O)_m(CF_2O)_nCF_2CH_2OH$ (m=22, n=19) and 7.1 g of 1,3-diallyl-5-(2-chloroethyl)isocyanurate were dissolved in a solvent mixture of m-hexafluoroxylene and diethylene glycol dimethyl ether. Then, 15 g of a 20 wt % aqueous solution of potassium hydroxide and 3 g of tetrabutyl ammonium bromide were added thereto and the components were heated under stirring. The completion of the reaction was confirmed by $^{19}F$-NMR and $^{1}H$-NMR. The reaction solution was concentrated and extracted, whereby a PFPE-containing compound (K) was obtained.

PFPE-Containing Compound (K):

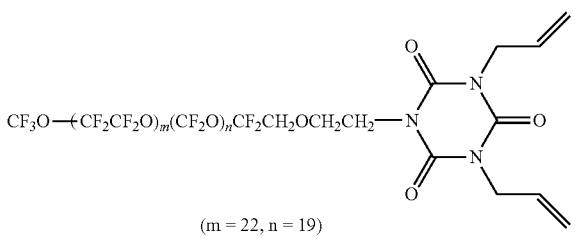

[Chem. 63]

$CF_3O\!-\!(CF_2CF_2O)_m(CF_2O)_nCF_2CH_2OCH_2CH_2\!-\!$ [triazine ring with two allyl groups]

(m = 22, n = 19)

Then, 9.6 g of the following PFPE-containing compound (L) containing trimethoxysilyl groups at ends was obtained in the same manner as in Example 7, except that the PFPE-containing compound (C) in Example 7 was changed to the PFPE-containing compound (K).

PFPE-Containing Compound (L):

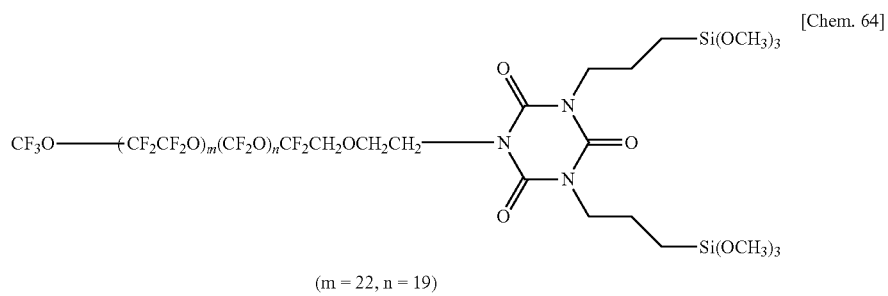

[Chem. 64]

$CF_3O\!-\!(CF_2CF_2O)_m(CF_2O)_nCF_2CH_2OCH_2CH_2\!-\!$ [triazine ring with two $-CH_2CH_2CH_2Si(OCH_3)_3$ groups]

(m = 22, n = 19)

Example 12: Method of Producing Perfluoropolyether (PFPE)-Containing Compound (N)

First, 2.0 g of 1,3-diallyl isocyanurate was dissolved in a solvent mixture of m-hexafluoroxylene and dimethyl formamide. Then, 1.0 g of potassium carbonate was added thereto and the components were heated under stirring. Further, 4.0 g of $CF_3O\!-\!(CF_2CF_2O)_m(CF_2O)_nCF_2CH_2$-trifluoromethane sulfonate (m=22, n=19) dissolved in m-hexafluoroxylene was added thereto and the heating under stirring was continued. The completion of the reaction was confirmed by $^{19}F$-NMR and $^{1}H$-NMR. Pure water was added to the reaction solution and the resulting liquid was separated, whereby a PFPE-containing compound (M) was obtained.

PFPE-Containing Compound (M):

[Chem. 65]

$CF_3O\!-\!(CF_2CF_2O)_m(CF_2O)_nCF_2CH_2\!-\!$ [triazine ring with two allyl groups]

(m = 22, n = 19)

Then, 9.8 g of the following PFPE-containing compound (N) containing trimethoxysilyl groups at ends was obtained in the same manner as in Example 7, except that the PFPE-containing compound (C) in Example 7 was changed to the PFPE-containing compound (M).

PFPE-Containing Compound (N):

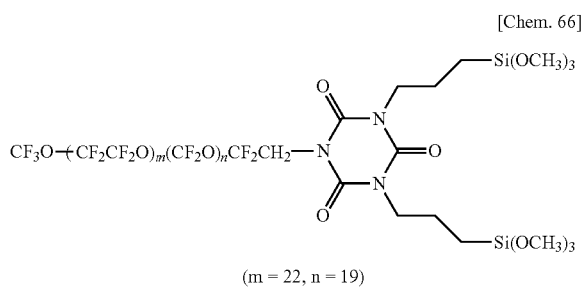

[Chem. 66]

(m = 22, n = 19)

Example 13: Method of Producing Perfluoropolyether (PFPE)-Containing Compound (P)

First, 10.0 g of the PFPE-containing compound (C), 40 g of m-hexafluoroxylene, 0.04 g of triacetoxymethylsilane, and 1.93 g of trichlorosilane were stirred at 10° C. for 30 minutes. Then, 0.115 ml of a xylene solution containing 2% Pt complex of 1,3-divinyl-1,1,3,3-tetramethyldisiloxane was added thereto and the components were heated and stirred for four hours. The volatile component was evaporated under reduced pressure, and 15 g of m-hexafluoroxylene was added thereto. Further, 22 ml of a tetrahydrofuran solution containing 1.0 mol/L of allyl magnesium chloride was added thereto in an ice bath. The components were warmed up to room temperature and then stirred at this temperature for 10 hours. The product was cooled down to 5° C. Then, 3 ml of methanol, followed by perfluorohexane were added thereto. The components were stirred for 30 minutes, and the perfluorohexane layer was collected using a separation funnel. Then, the volatile component was evaporated under reduced pressure, whereby 9.4 g of a PFPE-containing compound (O) containing allyl groups at ends was obtained.

PFPE-Containing Compound (O):

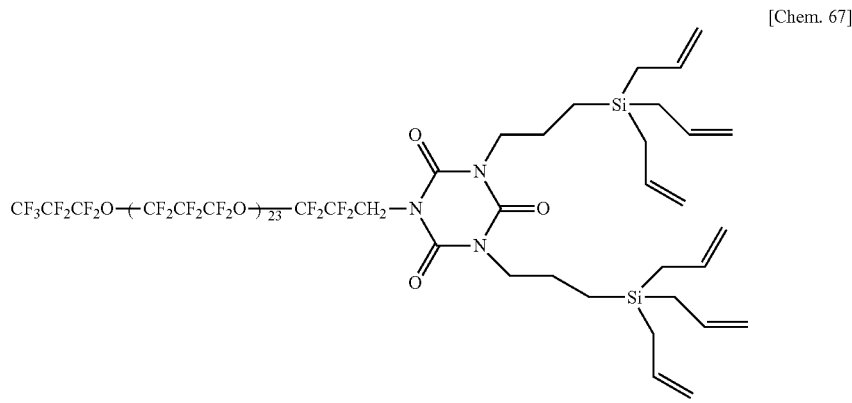

[Chem. 67]

Next, 9.0 g of the PFPE-containing compound (O), 30 g of m-hexafluoroxylene, 0.08 g of triacetoxymethylsilane, and 5.60 g of trichlorosilane were stirred at 10° C. for 30 minutes. Then, 0.297 ml of a xylene solution containing 2% Pt complex of 1,3-divinyl-1,1,3,3-tetramethyldisiloxane was added thereto and the components were heated and stirred for four hours. The volatile component was evaporated under reduced pressure, and a solution mixture of 0.57 g of methanol and 14.1 g of trimethyl orthoformate was added and the components were heated and stirred for three hours. The resulting product was purified, whereby 9.1 g of the following PFPE-containing compound (P) containing trimethoxysilyl groups at ends was obtained.

PFPE-Containing Compound (P):

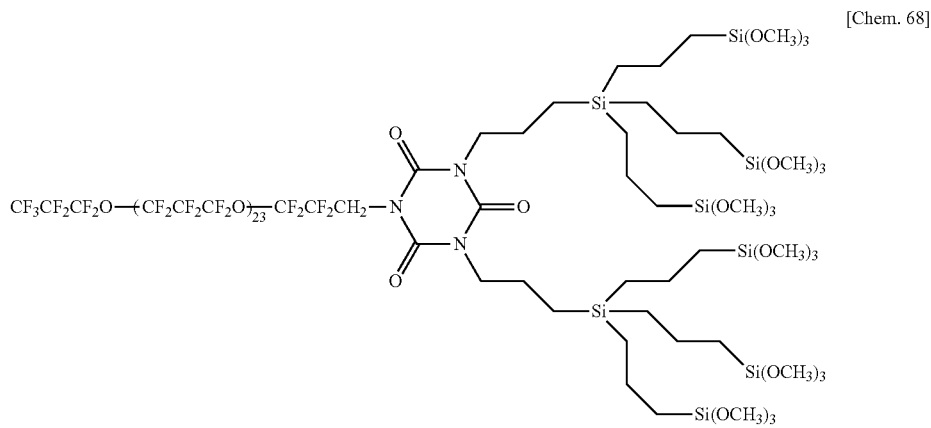

Example 14: Method of Producing Perfluoropolyether (PFPE)-Containing Compound (R)

First, 10.0 g of the PFPE-containing compound (M), 45 g of m-hexafluoroxylene, 0.04 g of triacetoxymethylsilane, and 1.41 g of dichloromethylsilane were stirred at 10° C. for 30 minutes. Then, 0.136 ml of a xylene solution containing 2% Pt complex of 1,3-divinyl-1,1,3,3-tetramethyldisiloxane was added thereto and the components were heated and stirred. The volatile component was evaporated. Then, 15 ml of vinyl magnesium chloride (1.6 M THF solution) was added thereto and the components were stirred at room temperature. The resulting product was purified, whereby 9.5 g of the following PFPE-containing compound (Q) containing methyl divinyl silyl groups at ends was obtained.

PFPE-Containing Compound (Q):

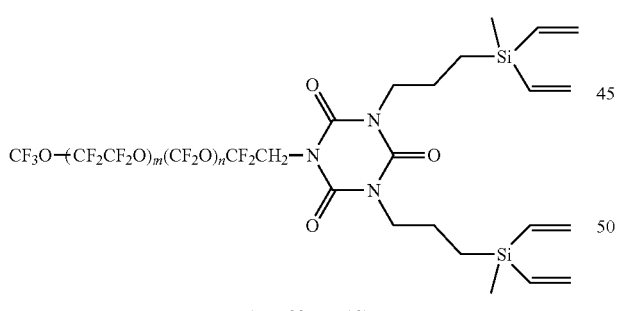

(m = 22, n = 19)

Next, 9.5 g of the PFPE-containing compound (Q), 42 g of m-hexafluoroxylene, 0.04 g of triacetoxymethylsilane, and 2.30 g of trichlorosilane were stirred at 10° C. for 30 minutes. Then, 0.230 ml of a xylene solution containing 2% Pt complex of 1,3-divinyl-1,1,3,3-tetramethyldisiloxane was added thereto and the components were heated and stirred for four hours. The volatile component was evaporated. Then, a solution mixture of 0.30 g of methanol and 7.56 g of trimethyl orthoformate was added and the components were heated and stirred. The resulting product was purified, whereby 9.6 g of the following PFPE-containing compound (R) containing trimethoxysilyl groups at ends was obtained.

PFPE-Containing Compound (R):

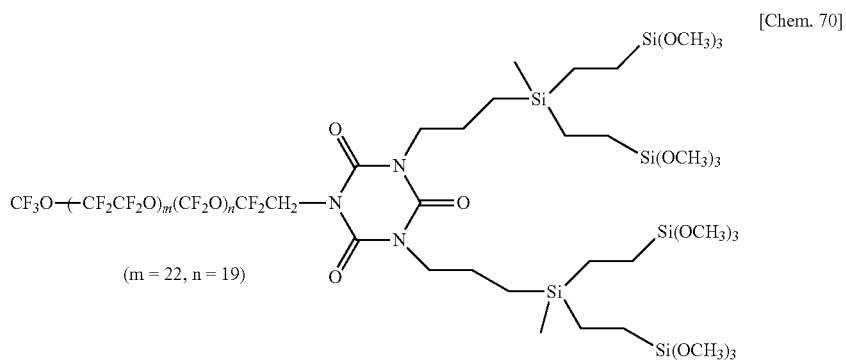

[Chem. 70]

Examples 15 to 22

The PFPE-containing compounds (G), (H), (I), (J), (L), (N), (P), and (R) obtained in Examples 7 to 14, respectively, were separately dissolved in hydrofluoroether (Novec HFE-7300, 3M) so as to be at a concentration of 1 mass %, whereby surface treatment agents (1) to (8) were prepared.

Comparative Examples 3 to 5

Comparative surface treatment agents (1) to (3) were prepared in the same manner as in Examples 15 to 22, except that the PFPE-containing compounds (G), (H), (I), (J), (L), (N), (P), and (R) were changed to any of the following control compounds (1) to (3).

Control Compound (1):

   [Chem. 71]

Control Compound (2):

   [Chem. 72]

Control Compound (3):

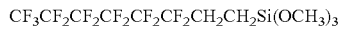   [Chem. 73]

The surface treatment agents (1) to (8) and the comparative surface treatment agents (1) to (3) prepared above were separately applied to a chemically strengthened glass ("Gorilla" Glass, Corning Inc., thickness 0.7 mm) using a spin coater.

The spin coating was performed at 300 revolutions/min for three seconds and 2000 revolutions/min for 30 seconds. The substrates coated were heated in the atmosphere in a constant temperature chamber at 140° C. for 30 minutes, whereby cured films were formed.

<Evaluation of Characteristics of Cured Film>
(Initial Evaluation)

At first, as initial evaluation, the static contact angle of each cured film with water was determined before any object was brought into contact with the surface thereof.
(Evaluation after Wiping with Ethanol)

Next, the cured film was wiped five times in a reciprocative manner with KimWipes (trade name, Jujo Kimberly Co., Ltd.) sufficiently impregnated with ethanol. The film was then dried before measurement of the static contact angle with water.
(Fingerprint Deposition Performance)

A finger was pushed against the cured film, and the ease of depositing a fingerprint was visually evaluated. The evaluation was based on the following criteria.

Good: A fingerprint was less likely to deposit on the cured film, or even when a fingerprint was deposited, it was difficult to see.

Fair: A fingerprint was less deposited, but this fingerprint was easily observed.

Poor: A fingerprint was clearly deposited similarly to the case of an untreated glass substrate.
(Ease of Wiping Off Fingerprint)

After the above fingerprint deposition test, the fingerprint deposited was wiped off five times in a reciprocative manner with KimWipes (trade name, Jujo Kimberly Co., Ltd.). The ease of wiping off the fingerprint deposited was visually observed. The evaluation was based on the following criteria.

Good: The fingerprint was completely wiped off.

Fair: The mark of wiping off the fingerprint remained.

Poor: The mark of wiping off the fingerprint spread and was difficult to remove.

The results of the respective evaluations are shown in Table 2.

TABLE 2

| | Static contact angle with water (degree) | | | | | | | | | | |
|---|---|---|---|---|---|---|---|---|---|---|---|
| | Example 15 | Example 16 | Example 17 | Example 18 | Example 19 | Example 20 | Example 21 | Example 22 | Comparative Example 3 | Comparative Example 4 | Comparative Example 5 |
| Initial | 114 | 114 | 114 | 114 | 115 | 115 | 115 | 115 | 113 | 105 | 105 |
| After wiping with ethanol | 114 | 114 | 114 | 114 | 115 | 115 | 115 | 115 | 112 | 103 | 103 |
| Fingerprint deposition performance | Good | Good | Good | Good | Good | Good | Good | Good | Good | Fair | Fair |

TABLE 2-continued

| | Static contact angle with water (degree) | | | | | | | | | | |
|---|---|---|---|---|---|---|---|---|---|---|---|
| | Example 15 | Example 16 | Example 17 | Example 18 | Example 19 | Example 20 | Example 21 | Example 22 | Comparative Example 3 | Comparative Example 4 | Comparative Example 5 |
| Ease of wiping off fingerprint | Good | Good | Good | Good | Good | Good | Good | Gocd | Fair | Poor | Poor |

Table 2 demonstrates that the cured films of Examples 15 to 22 showed high initial water repellency, showed no change even after wiping with ethanol, and showed very good evaluation results about the fingerprint deposition performance and the ease of wiping off fingerprint.

The invention claimed is:

1. A compound represented by the following formula (1):

[Chem. 1]

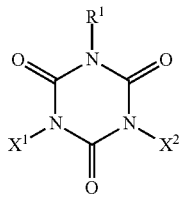

wherein $R^1$ is a monovalent organic group containing a polyether chain; $X^1$ and $X^2$ are each individually a monovalent group; and the polyether chain is a chain represented by the following formula:

$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein one of m11 or m12 is an integer of 1 or greater; and the other of m11 and m12, m13, m14, m15, and m16 are each individually an integer of 0 or 1 or greater; $X^{10}$s are each individually H, F, or Cl; the repeating units are present in any order; and the sum of m11 to m16 is an integer of 10 or greater, $R^1$ being other than those containing a urethane bond.

2. The compound according to claim 1, wherein at least one or both of $X^1$ and $X^2$ are each individually a monovalent organic group containing a polyether chain, and the polyether chain is a chain represented by the following formula:

$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein m11, m12, m13, m14, m15, and m16 of the polyether chains of $X^1$ and $X^2$ are each individually an integer of 0 or 1 or greater; $X^{10}$s are each individually H, F, or Cl; and the repeating units are present in any order.

3. The compound according to claim 1, wherein $X^1$ is a monovalent crosslinkable group.

4. The compound according to claim 1, wherein $X^2$ is a monovalent crosslinkable group.

5. The compound according to claim 1, wherein $X^1$ and $X^2$ are each individually a monovalent crosslinkable group.

6. The compound according to claim 1, wherein $X^1$ is a monovalent crosslinkable group containing a polyether chain, and the polyether chain is a chain represented by the following formula:

$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein m11, m12, m13, m14, m15, and m16 of the polyether chain of $X^1$ are each individually an integer of 0 or 1 or greater; $X^{10}$s are each individually H, F, or Cl; and the repeating units are present in any order.

7. The compound according to claim 1, wherein $X^2$ is a monovalent crosslinkable group containing a polyether chain, and the polyether chain is a chain represented by the following formula:

$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein m11, m12, m13, m14, m15, and m16 of the polyether chain of $X^2$ are each individually an integer of 0 or 1 or greater; $X^{10}$s are each individually H, F, or Cl; and the repeating units are present in any order.

8. The compound according to claim 1, wherein $X^1$ and $X^2$ are each individually a monovalent crosslinkable group containing a polyether chain, and the polyether chain is a chain represented by the following formula:

$$-(OC_6F_{12})_{m11}-(OC_5F_{10})_{m12}-(OC_4F_8)_{m13}-(OC_3X^{10}{}_6)_{m14}-(OC_2F_4)_{m15}-(OCF_2)_{m16}-$$

wherein m11, m12, m13, m14, m15, and m16 of the polyether chains of $X^1$ and $X^2$ are each individually an integer of 0 or 1 or greater; $X^{10}$s are each individually H, F, or Cl; and the repeating units are present in any order.

9. The compound according to claim 3, wherein the crosslinkable group is at least one crosslinkable group selected from the group consisting of a monovalent Si-containing group, an acryloyl group, a methacryloyl group, an epoxy group, a glycidyl group, an oxetane group, an isocyanate group, a vinyl group, an allyl group, a vinyloxy group, a carboxyl group, a mercapto group, an amino group, a hydroxy group, a phosphonyl group, a cyclic acid anhydride group, a lactone group, a lactam group, a —OC(O)Cl group, a triazine group, an imidazole group, a conjugated olefin group, an acetylene group, a diazo group, an aldehyde group, a ketone group, an alkylboron group, an alkylaluminum group, an alkyltin group, an alkylgermanium group, an alkylzircon group, and a monovalent group containing any of these groups.

10. The compound according to claim 1, wherein $X^1$ is at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

11. The compound according to claim 1,
wherein $X^2$ is at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

12. The compound according to claim 1,
wherein $X^1$ and $X^2$ are each individually at least one selected from the group consisting of H, an alkyl group, a halogenated alkyl group, an alkyl ester group, a halogenated alkyl ester group, an alkyl ether group, a halogenated alkyl ether group, an alkyl amide group, a halogenated alkyl amide group, a uril group, a halogenated uril group, a urea group, a halogenated urea group, —OCOOR$^j$, wherein R$^j$ is an alkyl group or a halogenated alkyl group, —CONR$^k$COR$^l$, wherein R$^k$ and R$^l$ are each individually H, an alkyl group, or a halogenated alkyl group, a glycan-containing group, an alkylene polyether group, an arene group, a halogenated arene group, a heterocycle-containing group, an aryl group, a halogenated aryl group, a silicone residue other than those containing a reactive group, and a silsesquioxane residue other than those containing a reactive group.

* * * * *